(12) United States Patent
Tachikawa et al.

(10) Patent No.: US 7,427,276 B2
(45) Date of Patent: Sep. 23, 2008

(54) SYRINGE

(75) Inventors: Kouichi Tachikawa, Yamanashi (JP);
Shingo Koyama, Kanagawa (JP);
Hiromitsu Okabe, Tokyo (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 0 days.

(21) Appl. No.: 11/878,143

(22) Filed: Jul. 20, 2007

(65) Prior Publication Data

US 2007/0265580 A1 Nov. 15, 2007

Related U.S. Application Data

(62) Division of application No. 10/500,339, filed as application No. PCT/JP02/13688 on Dec. 26, 2002, now Pat. No. 7,261,704.

(30) Foreign Application Priority Data

Dec. 28, 2001 (JP) .............................. 2001-401906
Nov. 11, 2002 (JP) .............................. 2002-327465

(51) Int. Cl.
*A61M 5/00* (2006.01)
*A61M 5/178* (2006.01)
*A61M 5/315* (2006.01)

(52) U.S. Cl. ..................................... 604/208
(58) Field of Classification Search ................. 604/187, 604/210, 218, 211, 207, 220, 208, 222, 198, 604/110, 209, 140, 143, 195, 146
See application file for complete search history.

(56) References Cited

U.S. PATENT DOCUMENTS 2,585,815 A 2/1952 McLintock (Continued)

FOREIGN PATENT DOCUMENTS

| JP | 54-10177 | 1/1979 |
|---|---|---|
| JP | 62-119944 | 7/1987 |
| JP | 2-15502 | 4/1990 |
| JP | 5-500621 | 2/1993 |
| JP | 10-005333 | 1/1998 |

OTHER PUBLICATIONS

International Preliminary Examination Report.

*Primary Examiner*—Matthew F DeSanto
(74) *Attorney, Agent, or Firm*—Buchanan Ingersoll & Rooney PC

(57) ABSTRACT

A syringe with which an accurate amount of a liquid can be discharged by a simple operation.

The syringe 1 includes an outer tube 2, a gasket 3 slidable in the outer tube 2, a pusher 4 operable for moving the gasket 3, and a stopper 5 disposed to be slidable along the longitudinal direction of the pusher 4. The stopper 5 is fixed relative to the pusher 4 by the engagement of engaging portions, provided therein, with racks 47a, 47b formed on the pusher 4. When an operating portion 71 is depressed, the fixation condition is released, permitting regulation of the position of the stopper 5 on the pusher 4. When the depression on the operating portion 71 is canceled, the fixation condition is retained. When the pusher 4 is pressed in the tip end direction, a tip end face 66 of the stopper 5 comes into contact with a base end portion 28 of the outer tube 2, whereby the depth of insertion of the pusher 4 into the outer tube 2 is restricted, and a set amount of a chemical 100 is discharged through a diameter-reduced portion 22.

12 Claims, 18 Drawing Sheets

U.S. PATENT DOCUMENTS

| | | |
|---|---|---|
| 2,856,925 A | 10/1958 | Heimer et al. |
| 3,563,240 A | 2/1971 | Silver |
| 4,153,056 A | 5/1979 | Silver et al. |
| 4,246,898 A | 1/1981 | Travalent et al. |
| 5,215,533 A | 6/1993 | Robb |
| 5,385,558 A * | 1/1995 | Cottone et al. ............... 604/208 |
| 5,531,708 A * | 7/1996 | Woodruff .................... 604/208 |
| 7,261,704 B2 * | 8/2007 | Tachikawa et al. .......... 604/187 |

* cited by examiner

SYRINGE

This application is a divisional of U.S. application Ser. No. 10/500,339 filed on Feb. 11, 2005, which is a U.S. national stage of International Application No. PCT/JP02/13688 filed on Dec. 26, 2002.

TECHNICAL FIELD

The present invention relates to a syringe with which an accurate amount of a liquid can be discharged through a simple operation.

BACKGROUND ART

A syringe comprises an outer tube, a gasket inserted in the outer tube, and a pusher (plunger rod) connected to the gasket, and is used to discharge a liquid such as a chemical by pressing the pusher to slide the gasket in the outer tube toward the tip end thereof.

In this case, for discharging an accurate amount of the liquid, it is necessary to regulate the amount of movement of the gasket while looking at the graduations provided on the outer circumferential surface of the outer tube and to carefully operate the pusher.

In cases of the conventional syringes, however, the problem that the amount of the liquid discharged would be too large or too small is liable to be generated due to a misoperation (overpushing or insufficient pushing) of the pusher or misreading of the graduations.

As a syringe for solving such a problem, syringes in which the amount of movement of the pusher can be restricted have been proposed, for example, in Japanese Utility Model Publication No. Hei 2-15502 and Japanese Utility Model Laid-open No. Sho 62-119944.

In the syringe (syringe 10) described in Japanese Utility Model Publication No. Hei 2-15502, a stopper (regulation ring 56) is movable in the longitudinal direction by being rotated relative to a pusher (plunger 22). Upon an operation of pressing the pusher against an outer tube (hollow cylinder 2) in the condition where the stopper has been moved to a desired position of the pusher, the stopper comes into abutment on the base end of the outer tube, whereby the movement of the pusher is restricted. Incidentally, the symbols used here are the same as those described in the publication.

In the syringe described in the publication, however, a means for fixing the stopper relative to the pusher is not provided, and, therefore, the position of the stopper relative to the pusher may easily change, making it difficult to maintain the desired discharge amount of the liquid. In addition, since the stopper is moved by rotation relative to the pusher, the operation for moving the stopper is extremely intricate to perform.

On the other hand, in the syringe (syringe 1) described in Japanese Utility Model Laid-open No. Sho 62-119944, a stopper (stopper 3) is movable along the longitudinal direction of a pusher (piston 2). Upon an operation of pressing the pusher against an outer tube (cylinder 4) in the condition where the stopper has been moved to a desired position of the pusher, the stopper comes into abutment on the base end of the outer tube, whereby the movement of the pusher is restricted.

In the syringe described in the publication, however, the stopper is provided with a hole for passing the pusher therethrough, and the stopper is fixed relative to the pusher by the engagement of an engaging groove 5, formed in the outer circumferential surface of the pusher, with an edge portion of the hole. Therefore, a strong force is required for the operation of moving the stopper relative to the pusher. Incidentally, the symbols used here are the same as those described in the publication.

Accordingly, it is an object of the present invention to provide a syringe with which an accurate amount of a liquid can be discharged through a simple operation.

DISCLOSURE OF INVENTION

The above object can be attained by the present invention as follows.

Specifically, the above object can be attained by the inventions as set forth in the following paragraphs (1) to (26).

(1) A syringe including: an outer tube, a gasket slidable in the outer tube, a pusher inserted through an opening of a base end of the outer tube and operable for moving the gasket, a stopper disposed on the pusher to be slidable along the longitudinal direction of the pusher, fixing means for selecting and fixing the position of the stopper on the pusher, and an operating portion provided in the stopper for performing a pressing operation, a traction operation or a pinching operation, wherein the position of the stopper on the pusher can be regulated by releasing the fixation by the fixing means through an operation at the operating portion, and the depth of insertion of the pusher into the outer tube is restricted by abutment of the stopper on a portion of the outer tube.

(2) A syringe as set forth in the above paragraph (1), wherein the fixing means is returned to a fixation state by elasticity when the operation on the operating portion is released.

(3) A syringe as set forth in the above paragraph (1) or (2), wherein the fixing means includes a rack provided on the pusher and including a plurality of engaging recessed portions or engaging projected portions provided at a predetermined interval along the longitudinal direction of the pusher, and an engaging portion provided on the stopper to be displaceable between a state of being engaged with the rack and a state of being retracted from the rack, and the engaging portion is normally engaged with the rack and is retracted from the rack by an operation at the operating portion.

(4) A syringe as set forth in the above paragraph (3), wherein the fixing means includes a pressing portion operated in conjunction with the operating portion to be displaced between a first position for pressing the engaging portion to be engaged with the rack and a second position for releasing the pressing, and biasing means biasing the pressing portion to bring into the first position, and the fixing means is normally in such a state that the pressing portion is located in the first position and the engaging portion is engaged with the rack to fix the stopper, the fixing means being so operated that, when the operating portion is operated, the pressing portion is moved to the second position, whereby the engageing portion is retracted from the rack and a fixation of the stopper is released, and when the operation on the operating portion is released, the fixing means is returned into the state for fixation of the stopper by the biasing force of the biasing means.

(5) A syringe as set forth in the above paragraph (3), wherein the fixing means includes biasing means biasing the engaging portion to displace from a state of being retracted from the rack to a state of being engaged with the rack, the fixing means is normally in such a state that the engaging portion is engaged with the rack to fix the stopper, and the fixing means is so operated that, when the operating portion is operated, the engaging portion is retracted from the rack to release a fixation of the stopper, and when the operation on the operating portion is released, the fixing means is returned into the state for fixation of the stopper by the biasing force of the biasing means.

(6) A syringe as set forth in any of the above paragraphs (3) to (5), wherein the pusher includes a main body portion in such a shape that plate pieces are intersected in a cross form, and the rack is formed in a portion of the plate pieces.

(7) A syringe as set forth in any of the above paragraphs (3) to (6), wherein a pair of the racks are provided.

(8) A syringe as set forth in any of the above paragraphs (1) to (7), wherein the pusher includes a rail portion, and the stopper includes a slide portion slid along the rail portion, and the stopper is slid along the longitudinal direction of the pusher by guiding of the slide portion on the rail.

(9) A syringe as set forth in any of the above paragraphs (1) to (8), wherein the maximum width of the stopper is smaller than the maximum width of the pusher.

(10) A syringe as set forth in any of the above paragraphs (1) to (9), wherein the operating portion is operated by being pressed by a finger.

(11) A syringe as set forth in any of the above paragraphs (1) to (10), wherein the operating portion is operated by being pinched between fingers.

(12) A syringe including: an outer tube, a gasket slidable in the outer tube, a pusher inserted through an opening of a base end of the outer tube and operable for moving the gasket, a stopper provided on the pusher so that the stopper can be slid along the longitudinal direction of the pusher and the position of the stopper on the pusher can be regulated to a desired position, and an operating member provided to be displaceable relative to the stopper, the operating member performing an operation of fixing the stopper relative to the pusher by pressing a portion of the stopper against the pusher, wherein the depth of insertion of the pusher into the outer tube is restricted by abutment of the stopper on a portion of the outer tube.

(13) A syringe as set forth in the above paragraph (12), wherein either one or both of abutment surfaces of the stopper and the pusher are formed as rough surfaces or are formed of a material having a high frictional resistance.

(14) A syringe as set forth in the above paragraph (13), wherein the material having a high frictional resistance is an elastic material.

(15) A syringe as set forth in the above paragraph (13) or (14), wherein the pusher is provided with a pair of the abutment surfaces substantially parallel to each other.

(16) A syringe as set forth in the above paragraph (15), wherein the abutment surfaces of the pusher are opposed to each other.

(17) A syringe as set forth in the above paragraph (16), wherein the abutment surfaces of the pusher are on a same plane.

(18) A syringe as set forth in any of the above paragraphs (12) to (17), wherein the stopper includes a stopper main body, and a brake portion pressed against the pusher by an operation of the operating member.

(19) A syringe as set forth in the above paragraph (18), wherein the pressing of the brake portion against the pusher is performed by clamping of the brake portion between a portion of the operating member and the pusher.

(20) A syringe as set forth in the above paragraph (18), wherein the pressing of the brake portion against the pusher is performed by fitting a portion of the operating member between the stopper main body and the pusher so as to move the stopper main body in the direction for spacing away from the pusher.

(21) A syringe as set forth in any of the above paragraphs (18) to (20), wherein the operating member is turnable relative to the stopper main body.

(22) A syringe as set forth in any of the above paragraphs (18) to (21), wherein the operating member is slidable relative to the stopper main body.

(23) A syringe as set forth in any of the above paragraphs (12) to (22), wherein the pusher includes a rail portion for guiding the stopper, and a portion of the stopper is pressed against the rail portion.

(24) A syringe as set forth in any of the above paragraphs (1) to (23), wherein the pusher is provided thereon with graduations for indicating the position of the stopper corresponding to the amount of a liquid discharged.

(25) A syringe as set forth in the above paragraph (24), wherein the pusher includes positioning means for positioning the stopper at the position of 0 (zero) of the graduations.

(26) A syringe as set forth in any of the above paragraphs (1) to (25), wherein a chemical is preliminarily contained in a space surrounded by the outer tube and the gasket.

BEST MODE FOR CARRYING OUT THE INVENTION

Figure 1:
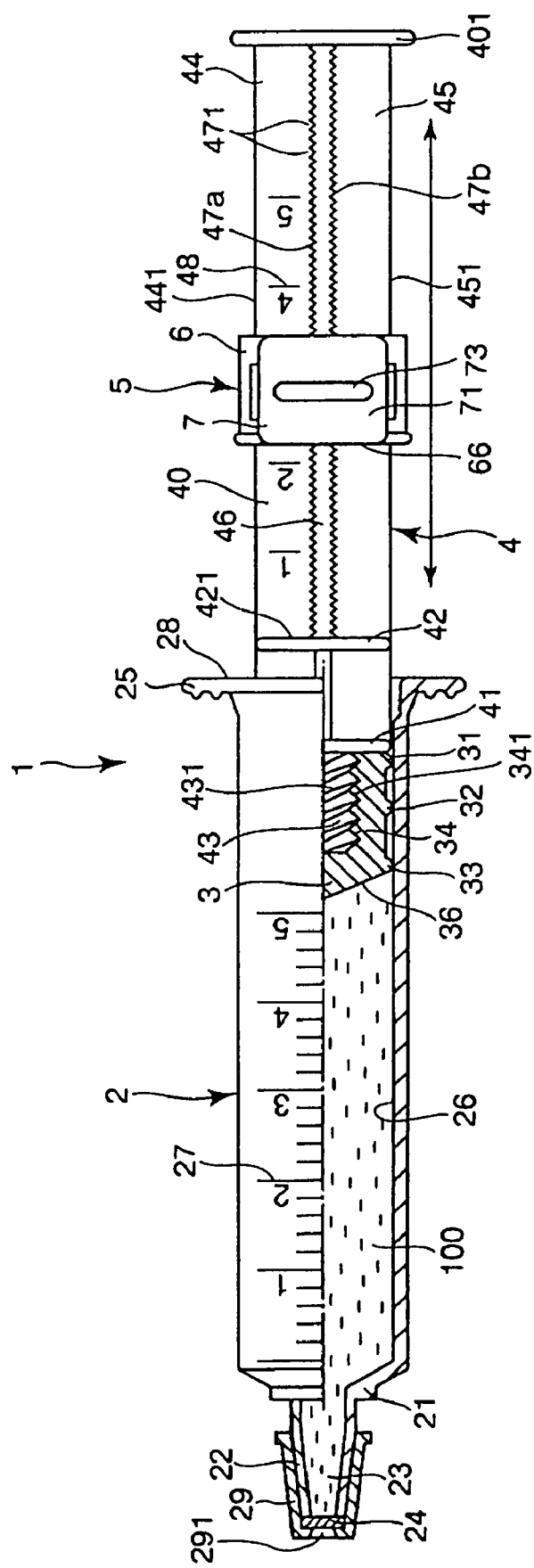
FIG. 1 is a partly vertical sectional view of a first embodiment of the syringe according to the present invention.

Now, the present invention will be described in detail below.

The syringe according to the present invention will be described in detail below, based on preferred embodiments shown in the drawings.

First Embodiment

Figure 2:
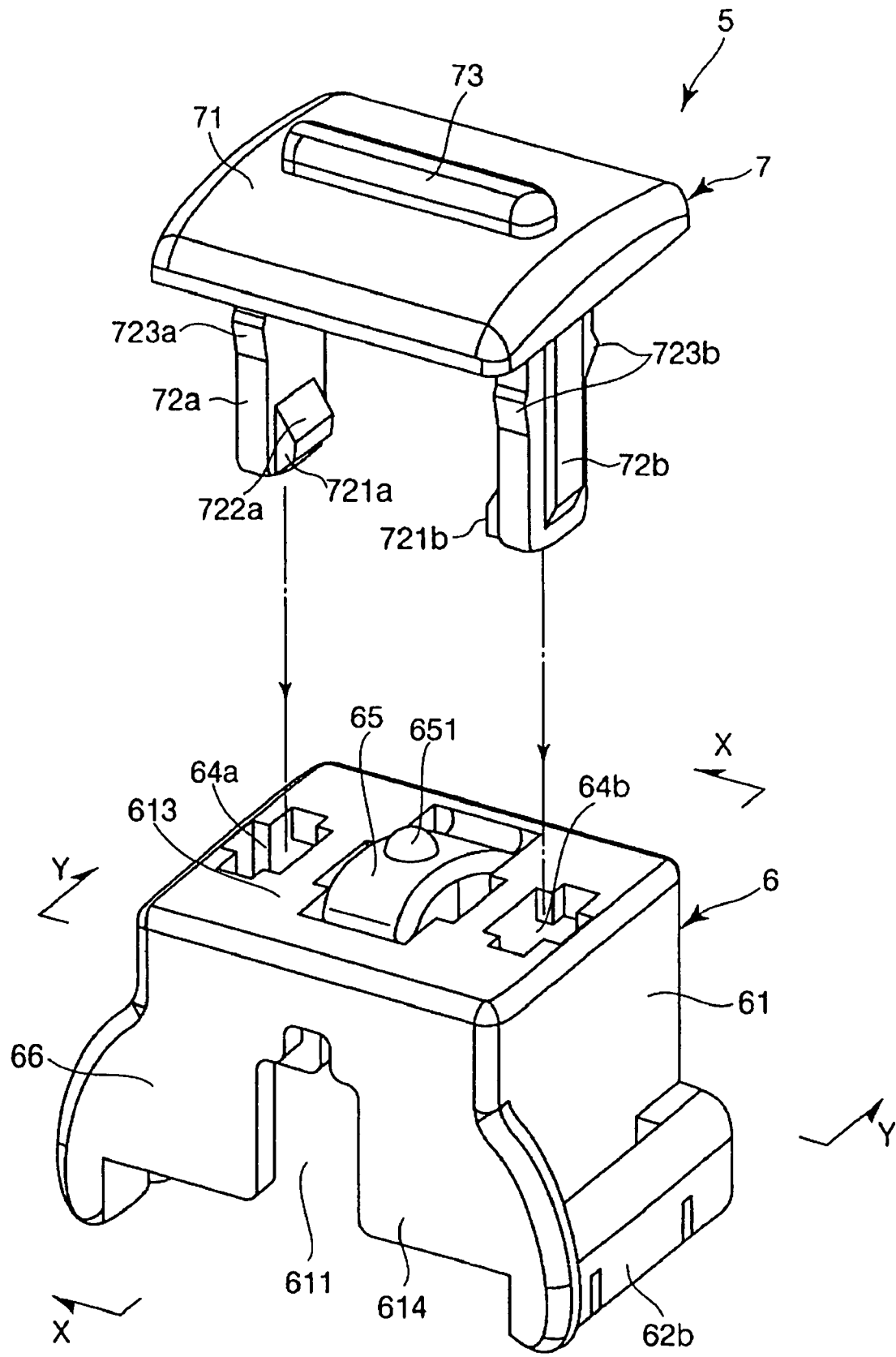
FIG. 2 is a perspective view (in an exploded state) of a stopper in the syringe shown in FIG. 1.
Figure 3:
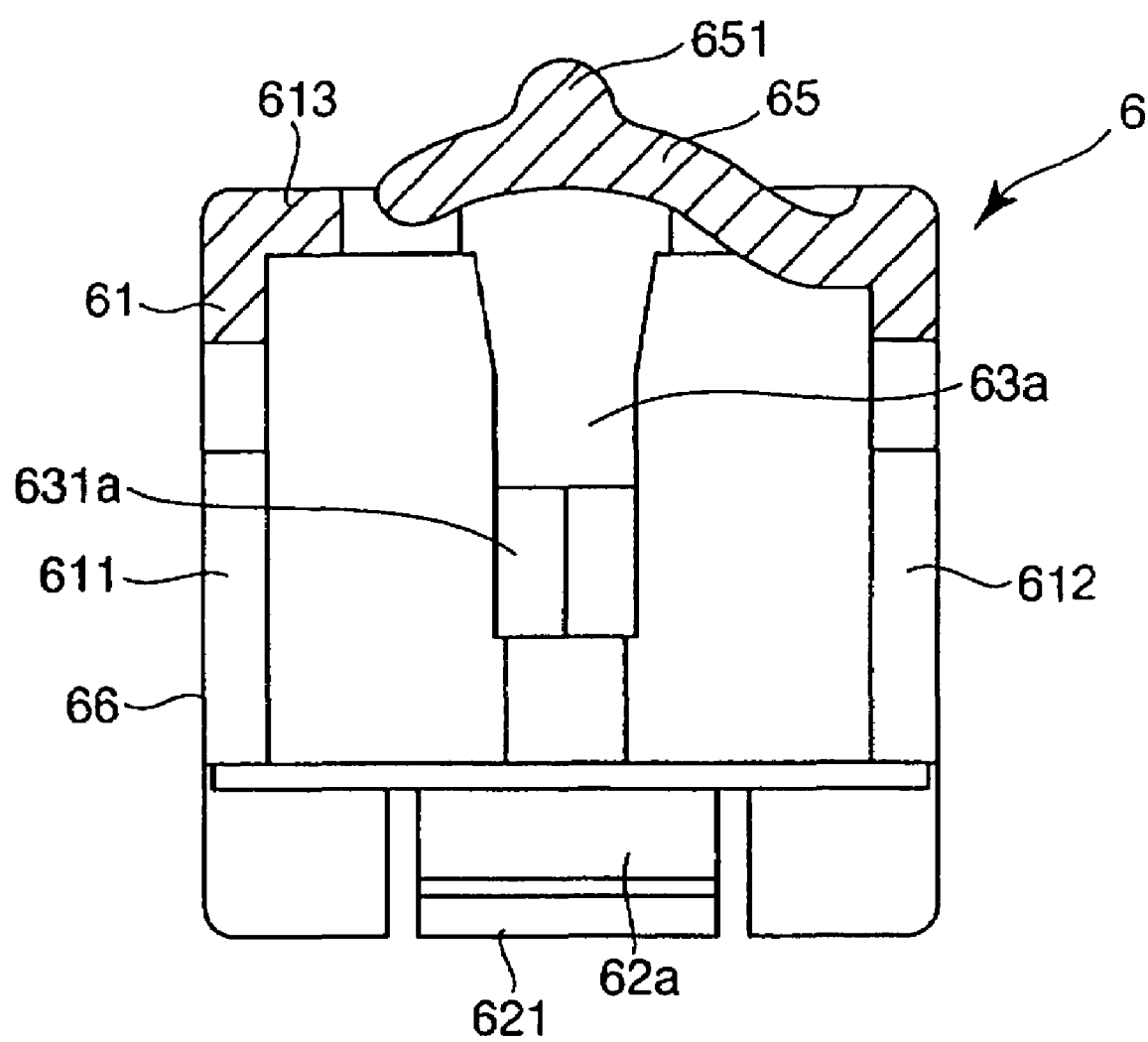
FIG. 3 is a sectional view along line X-X of FIG. 2.
Figure 4:
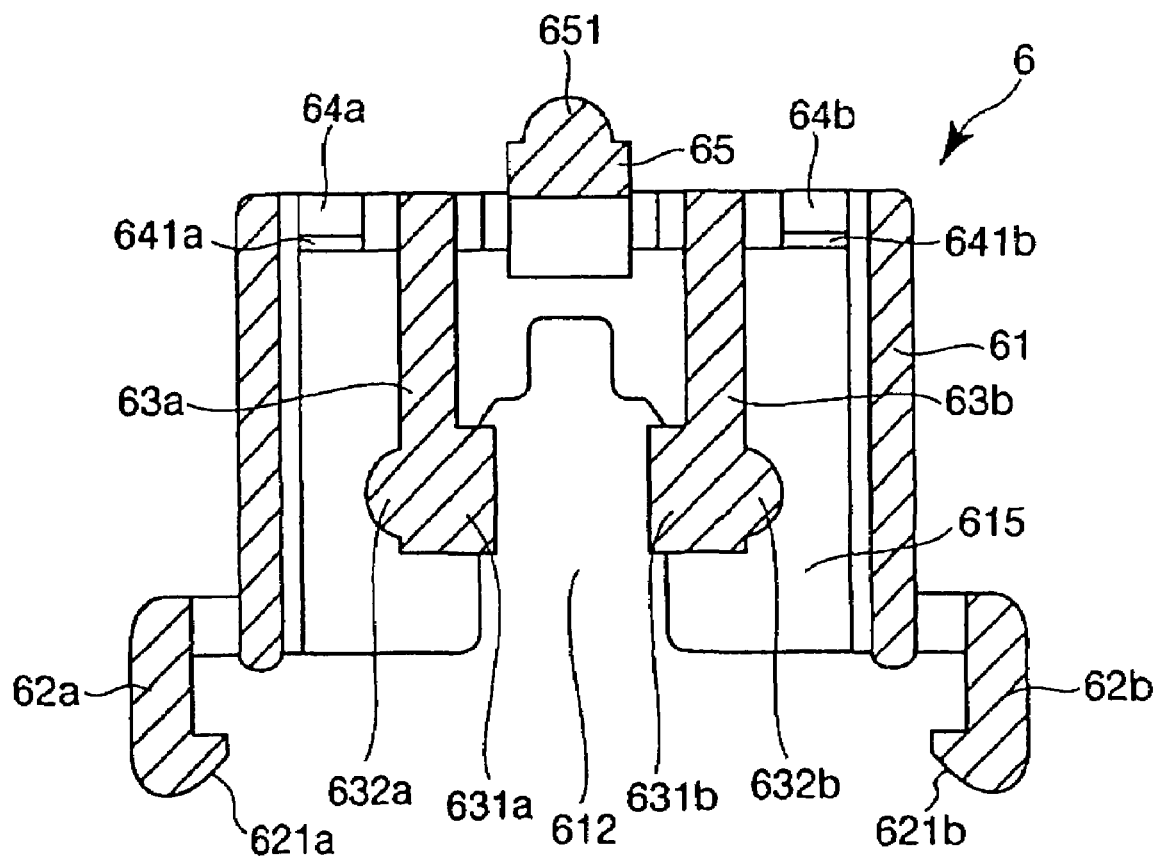
FIG. 4 is a sectional view along line Y-Y of FIG. 2.
Figure 5:
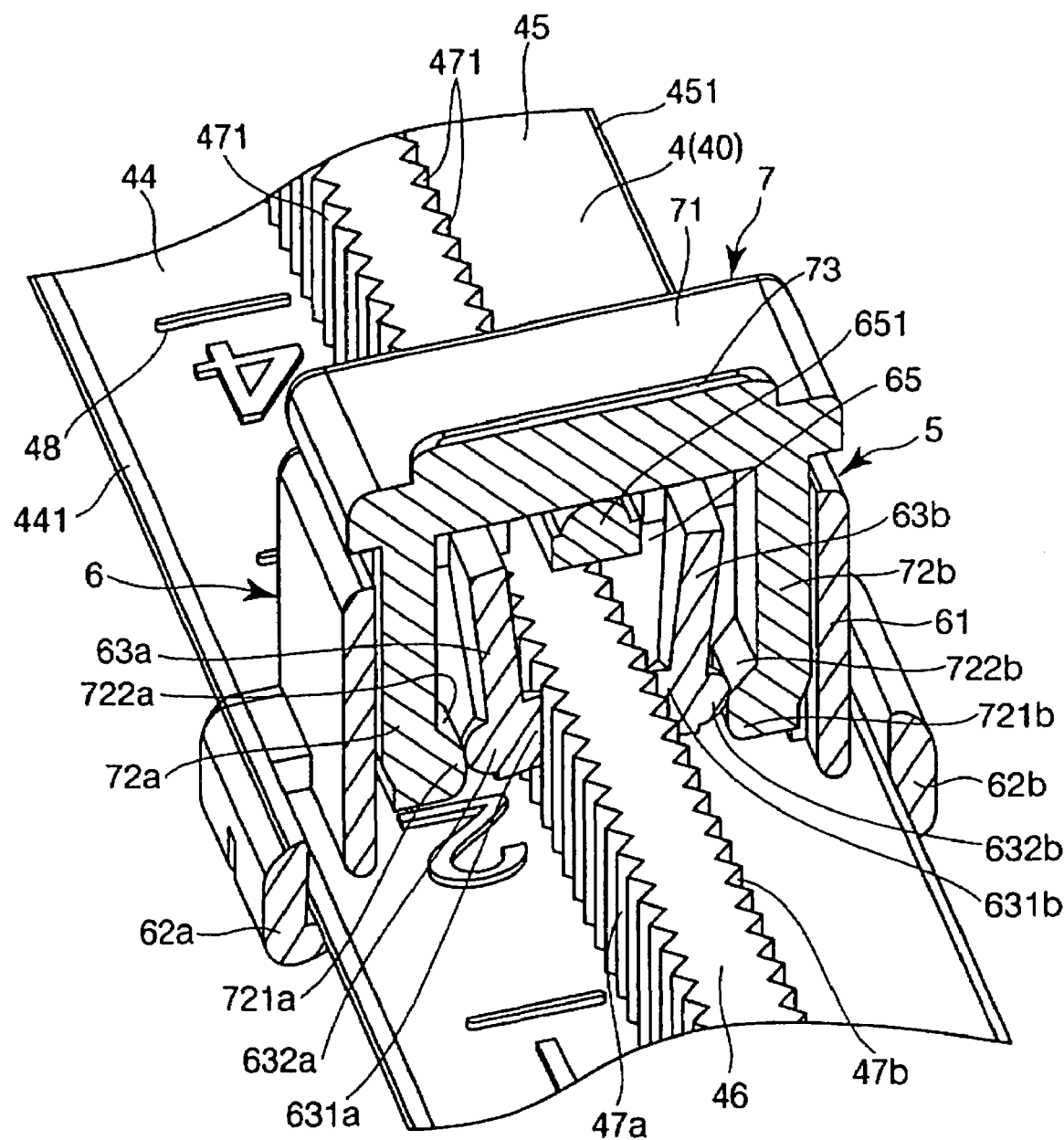
FIG. 5 is a partly sectional perspective view (in a state the stopper being fixed) showing a main body portion of a pusher and a stopper in the syringe shown in FIG. 1.
Figure 6:
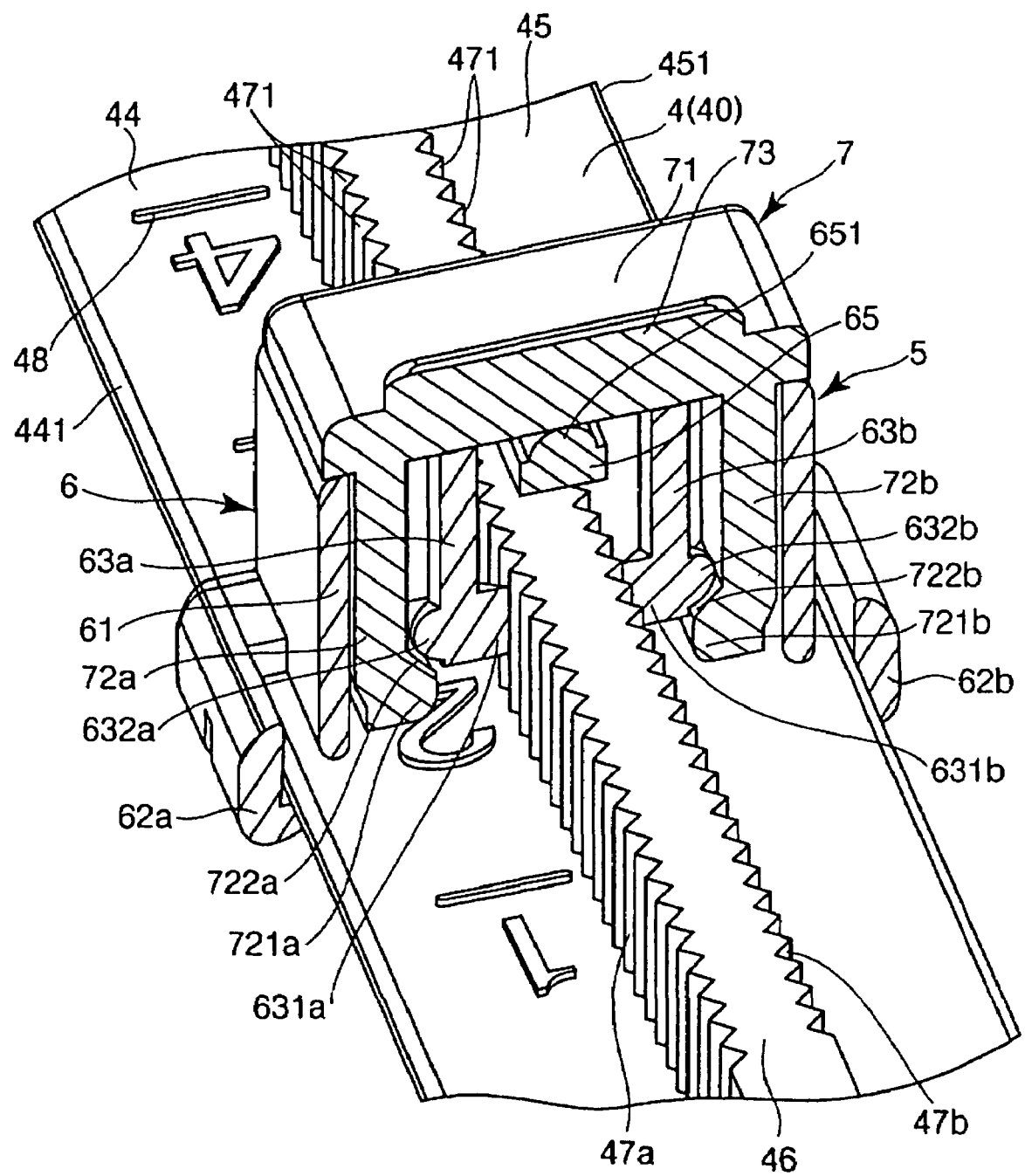
FIG. 6 is a partly sectional perspective view (in a state a fixation being released) showing the main body portion of the pusher and the stopper in the syringe shown in FIG. 1.

FIG. 1 is a partly vertical sectional view showing a first embodiment of the syringe according to the present invention, FIG. 2 is a perspective view (in an exploded state) of a stopper in the syringe shown in FIG. 1, FIG. 3 is a sectional view along line X-X of FIG. 2, FIG. 4 is a sectional view along line Y-Y of FIG. 2, and FIGS. 5 and 6 are partly sectional perspective views showing a main body portion of a pusher and a stopper in the syringe shown in FIG. 1. Incidentally, for convenience of description, the side of an outer tube of the syringe in FIG. 1 will be referred to as "the tip end", and the side of the pusher as "the base end"; the side of a second member of the stopper in FIG. 2 will be referred to as "upper", and the side of a first member as "lower"; the side of projected portions provided on a leaf spring of the first member in FIGS. 3 and 4 will be referred to as "upper", and the opposite side as "lower"; and the side of the stopper in FIGS. 5 and 6 will be referred to as "upper", and the side of the main body portion of the pusher as "lower".

The syringe 1 in this embodiment shown in FIG. 1 is a pre-filled syringe with the inside of the syringe being pre-filled with a chemical, and includes an outer tube (syringe outer tube)$_2$, a gasket 3 slidable in the outer tube 2, a pusher (plunger rod) 4 operable for moving the gasket 3, and a stopper 5 disposed to be slidable along the longitudinal direction of the pusher 4. The gasket 3 is connected to the tip end of the pusher 4. Now, the configurations of the individual portions will be described below.

The outer tube 2 is composed of a bottomed tubular member having a bottom portion 21 on the tip end side, and the bottom portion 21 is integrally provided at its central portion with a tubular diameter-reduced portion 22 which is reduced in diameter as compared with a body portion of the outer tube 2. The diameter-reduced portion 22 opens at its tip end portion, and, for example, a hub, a connector or the like (not shown) of a needle pipe is fitted in the opening and is used.

A base end portion of the diameter-reduced portion 22 may be provided with a male screw (lure lock screw) along the outer circumference thereof.

A film 24 formed of an elastic material, as a sealing member, is attached to the tip end of the diameter-reduced portion 22 so as to cover the opening at the tip end of the diameter-reduced portion 22, thereby sealing gas-tightly a lumen 23 of the diameter-reduced portion 22.

In addition, a bottomed tubular cap 29 having a bottom portion on the tip end side is fitted over and fixed to the outside surface of the diameter-reduced portion 22. The cap 29 is provided with an opening 291 at its tip end, and an outer circumferential portion of the film 24 is clamped between an edge portion of the opening 291 and the tip end face of the diameter-reduced portion 22, whereby the film 24 is fixed in a gas-tight (liquid-tight) manner.

Incidentally, the diameter-reduced portion 22, the film 24 and the cap 29 may be adhered to each other with an adhesive or fused to each other.

The film 24 can be punctured by a needle body such as a double ended needle. In this case, the form of the film 24 is not limited to the film-like form, as long as the film 24 can be punctured by a needle body; for example, the film 24 may be a block-form body (plug body).

As a material for constituting the film 24, for example, those materials which will be mentioned as constituent material of the gasket 3 later can be used.

Incidentally, the sealing member for sealing the tip end of the diameter-reduced portion 22 is not limited to the configuration shown in the figure; for example, the sealing member may be a thin film or the like (not shown).

Besides, the base end of the outer tube 2 is integrally provided with a plate-like flange 25 along the outer circumference thereof. At the time of, for example, an operation for moving the pusher 4 relative to the outer tube 2, the operation can be conducted with a finger put on the flange 25.

The material for constituting the outer tube 2 is particularly limited. Examples of the constituent material usable include various resins such as polyvinyl chloride, polyethylene, polypropylene, cyclic polyolefins, polystyrene, poly-(4-methylpentene-1), polycarbonate, acrylic resins, acrylonitrile-butadiene-styrene compolymer, polyesters such as polyethylene terephthalate and polyethylene naphthalate, butadiene-styrene copolymer, and polyamides (e.g., nylon 6, nylon 6,6, nylon 6,10, nylon 12). In terms of little moisture loss, the resins such as polypropylene, cyclic polyolefins, polyesters, and poly-(4-methylpentene-1), of the above examples are preferable.

Incidentally, the constituent material of the outer tube 2 preferably is substantially transparent, for securing visibility of the inside thereof.

A chemical 100 is contained liquid-tightly in the space surrounded by the outer tube 2 and the gasket 3. The form of the chemical 100 may be arbitrary; for example, the chemical 100 may be in a solid form (inclusive of powder form and granular form), a liquid form or the like. In this embodiment, a chemical in a liquid form will be described as a representative.

Examples of the chemical 100 include a variety of chemicals such as antitumor agents, anesthetics, stimulants, narcotics, carbohydrate injections such as glucose, electrolyte correction injections such as sodium chloride and potassium lactate, vitamin agents, vaccines, antibiotic injections, contrast media, steroid agents, protease inhibitors, lipid emulsions, etc., and also include distilled water, disinfectants, fluid foods, alcohols, etc.

The outer tube 2 is provided with graduations 27 on the outer circumferential surface thereof. This makes it possible to grasp the amount of the liquid contained in the syringe 1. In the configuration shown in the figure, the graduations 27 range from 0 to 5 mL.

The gasket 3 formed of an elastic material and slidable in the longitudinal direction of the outer tube 2 is contained in the outer tube 2.

The gasket 3 is provided at its outer circumferential portion with a plurality of annular projected portions 31, 32 and 33 over the entire circumference. The projected portions 31, 32 and 33 keep close contact with an inner circumferential surface 26 of the outer tube 2 during sliding, whereby the liquid-tightness can be securely maintained, and enhancement of slidability can be contrived.

In this embodiment, three projected portions 31, 32 and 33 are provided along the longitudinal direction of the syringe 1. Specifically, the projected portions 31, 32 and 33 are provided at a base end portion, an intermediate portion and a tip end portion of the gasket 3, respectively. In addition, a tip end surface 36 of the gasket 3 is a tapered surface whose diameter is gradually reduced toward the tip end.

Incidentally, in the present invention, the positions, the number, the cross-sectional shape and the like of the projected portions 31, 32 and 33 are not limited to the above-mentioned.

In addition, the gasket 3 is provided with a hollow portion 34 opening at the base end face thereof. A head portion 43 of the pusher 4 which will be described later is inserted (screw-engaged) into the hollow portion 34. The hollow portion 34 is provided with a female screw 341 at the inside surface thereof.

The material for constituting the gasket 3 is not particularly limited. Examples of the constituent material usable include elastic materials such as various rubber materials, e.g., natural rubber, butyl rubber, isoprene rubber, butadiene rubber, styrene-butadiene rubber, silicone rubber, etc., various thermoplastic elastomers based on polyurethane, polyester, polyamide, polyolefin, styrene or the like, and mixtures thereof.

Incidentally, it suffices that at least an outer circumferential portion of the gasket 3 is constituted of the above-mentioned elastic material. For example, there may be adopted a configuration in which the gasket 3 includes a core portion (not shown) constituted of a resin material and the elastic material is disposed to cover the outer circumference of the core portion. In this case, the female screw 341 is provided at the core portion.

To such a gasket 3 is connected (attached) the pusher 4 for movably operating the gasket 3 in the outer tube 2 in the longitudinal direction.

The pusher 4 includes a main body portion 40 in such a shape that plate pieces 44 and 46 are intersected in a cross form, and the main body portion 40 is provided at its base end with a flange-formed finger receiving portion 401. With the finger receiving portion 401 pressed by a finger or the like, the pusher 4 is moved in the tip end direction.

On the tip end side of the main body portion 40, a first flange 41 formed in a sword-guard like shape and a second flange 42 located on the base end side relative to the first flange 41 are provided integrally with the main body portion 40. The first flange 41 and the second flange 42 are disposed substantially in parallel to each other, at a predetermined interval of about 3 to 50 mm, for example.

Further, on the tip end side relative to the first flange 41, the pusher 4 is provided with a head portion (connection portion) 43 inserted in the hollow portion 34 of the gasket 3 and connected to the gasket 3.

The head portion 43 is provided at its outer circumference with a male screw 431 which is screw-engageable with the female screw 341 formed at the inside surface of the hollow portion 34. By screw engagement of the male screw 431 and the female screw 341 with each other, the gasket 3 and the pusher 4 are connected to each other. In such a connected condition, the tip end face of the first flange 41 is in contact or close contact with the base end face of the gasket 3.

Incidentally, in the present invention, the connection structure between the gasket 3 and the pusher 4 is not limited to the screw engagement; for example, attachment such as adhesion, fusing, etc., fitting, loose fitting and the like may also be adopted for the connection.

The material for constituting the pusher 4 is not particularly limited; for example, the same materials as those mentioned above as the constituent material of the outer tube 2 can be used.

In addition to the above-described configuration, the syringe 1 according to the present invention includes a stopper (insertion depth restrictive member) 5 disposed to be movable along the longitudinal direction of the pusher 4, and a fixing means for selecting (regulating) and fixing the position of the stopper 4 on the pusher 4. As shown in FIG. 1, the stopper 5 is disposed on the main body 40 on the base end side relative to the second flange 42.

In the syringe 1, at the time of discharging the chemical 100 by pressing the pusher 4 to move in the direction of the tip end, a tip end surface 66 of the stopper 5 abuts on a base end portion (base end face) 28 of the outer tube 2, whereby the depth of insertion of the pusher 4 into the outer tube 2 is restricted. This makes it possible to discharge an accurate amount of the chemical 100. Now, the configuration of the stopper 5 and the fixing means will be described in detail below.

As shown in FIG. 2, the stopper 5 is composed of a first member 6, and a second member 7. The first member 6 and the second member 7 are each substantially symmetric on the left and right sides in FIG. 2.

The first member 6 includes a roughly box-like casing 61 opened on the lower side in FIG. 2. As shown in FIG. 4, the casing 61 is provided, at its left and right lower end portions in the figure, with projected slide portions 62a and 62b roughly angular U-shaped in section. The first member 6 is slidable (movable) along the longitudinal direction of the pusher 4, with the slide portions 62a and 62 being slid on rail portions 441 and 451 provided on the pusher 4.

In this embodiment, as shown in FIG. 1, edge portions of the two parallel plate pieces 44 and 45, of the four plate pieces 44, 45, 46 and 46 intersecting in a cross form to constitute the main body portion 40 of the pusher 4, constitute the rail portions 441 and 451, respectively. As shown in FIG. 5, the rail portions 441 and 451 are inserted respectively into the inside of the slide portions 62a and 62b, and the inside surfaces of the slide portions 62a and 62b are slid along the rail portions 441 and 451, whereby the first member 6 is guided along the longitudinal direction of the pusher 4.

As shown in FIG. 4, the lower surfaces of the slide portions 62a and 62b, on the inside, are inclined tapered surfaces 621a and 621b, respectively. This ensures that, at the time of mounting the first member 6 to the pusher 4 in the process of assembling the syringe 1, the rail portions 441 and 451 are slid on the tapered surfaces 621a and 621b, whereby the slide portions 62a and 62b are elastically deformed in the manner of being pressed wider to the outside, permitting easy mounting.

As shown in FIGS. 2 and 4, a tip end wall 614 and a base end wall 615 of the casing 61 are respectively provided in grooves 611 and 612 in central portions thereof. In the condition where the first member 6 is mounted to the pusher 4, the plate piece 46 orthogonal to the plate pieces 44 and 45 of the main body portion 40 is inserted in the grooves 611 and 612.

As shown in FIGS. 1 and 5, side surfaces of the plate piece 46 are provided with racks 47a and 47b including a plurality of engaging recessed portions 471 formed at a predetermined interval along the longitudinal direction of the pusher 4. Engaging portions 63a and 63b provided in the first member 6 are engaged with the racks 47a and 47b, whereby the stopper 5 is fixed to the pusher 4.

In this embodiment, a pair of the racks 47a, 47b and a pair of engaging portions 63a, 63b are provided. This enables securer fixation of the stopper 5 to the pusher 4. The pair of racks 47a and 47b are provided on both side surfaces of the plate piece 46, respectively.

The interval (pitch) of the engaging recessed portions 471 in the racks 47a, 47b is not particularly limited, and is appropriately set according to the volume of the syringe 1 or the like. For example, the interval (pitch) can be set to correspond to one of increments (or decrements) of 0.1 mL, 0.2 mL, 0.5 mL, 1 mL, 5 mL, 10 mL and the like of the amount of the liquid discharged from the syringe 1. In the configuration shown in the figures, the interval of the engaging recessed portions 471 corresponds to a discharge amount increment (or decrement) of 0.1 mL. In such a case, the pitch of the engaging recessed portions 471 is determined in relation to the diameter of the outer tube 2 of the syringe 1. In view of enabling minute regulation, the pitch is preferably not more than 4 mm, and more preferably not more than 2 mm.

In the configuration shown in the figures, the engaging recessed portions 471 are composed of roughly V-shaped grooves. This enables the stopper 5 to be fixed accurately, without chattering. In addition, the plurality of engaging recessed portions 471 are formed adjacent to each other, so that the racks 47a and 47b are serrate.

Incidentally, in the present invention, the shape of the engaging recessed portions 471 is not limited to that shown in the figures. For example, the engaging recessed portions 471 may be composed of U-shaped, roughly angular U-shape or semicircular grooves, or holes or the like. Besides, the engaging recessed portions 471 are not limited to those which are formed adjacent to each other as shown in the figures, and may be intermittently formed at a predetermined interval.

As shown in FIG. 5, a pair of engaging portions 63a and 63b capable of engagement with the racks 47a and 47b are provided in the inside of the casing 61.

As shown in FIG. 4, the engaging portions 63a and 63b are formed in the shape of arms projecting from an upper wall 613 (see FIG. 2) of the casing 61 toward the inside of the casing 61.

As shown in FIG. 5, the plate piece 46 is located between the engaging portions 63a and 63b. On the lower end side of the engaging portions 63a and 63b, projections 631a and 631b formed in a wedge shape (V shape) corresponding substantially to the shape of the engaging recessed portions 471 are provided to project toward the inside, and the projections 631a and 631b are respectively inserted into the engaging recessed portions 471 of the racks 47a and 47b, whereby both of them are engaged with each other.

The engaging portions 63a and 63b are provided with roughly hemispherical projected portions 632a and 632b on the opposite side (outside) of the projections 631a and 631b.

In addition, as shown in FIG. 2, the upper wall 613 is provided with holes 64a and 64b on the outside of the locations of the engaging portions 63a and 63b, respectively.

Besides, as shown in FIG. 3, the upper wall 613 is integrally provided with a cantilever leaf spring (biasing means) 65 at a central portion thereof. The leaf spring 65 has a curved shape, and is provided at its central portion with a roughly hemispherical projected portion 651 projecting to the outside (upper side). When the leaf spring 65 is in a natural state, the projected portion 651 is in the state of protruding from the upper wall 613; when the leaf spring 65 is deflected downwards, the projected portion 651 sinks into the inside of the casing 61.

As shown in FIG. 2, the second member 7 includes a roughly plate-like operating portion 71, a pair of pressing portions 72a and 72b projecting in an arm shape from the lower surface of the operating portion 71, and a rib 73 formed on the upper surface of the operating portion 71.

The operating portion 71 is a portion to be depressed by a finger, i.e., it functions as a pushbutton. The rib 73 displays an anti-slipping effect at the time of depressing the operating portion 71 by a finger. The pressing portions 72a and 72b display the function of respectively pressing the engaging portions 63a and 63b to the inside.

As shown in FIG. 5, the second member 7 is mounted to the first member 6 in the condition where the pressing portions 72a and 72b are inserted respectively in the holes 64a and 64b (see FIG. 2). In this condition, claws 723a and 723b formed on the pressing portions 72a and 72b are engaged with claws 641a and 641b formed on the inside surfaces of the holes 64a and 64b, whereby the second member 7 is prevented from slipping off from the first member 6 (see FIGS. 2 and 4).

As shown in FIGS. 2 and 5, projected portions 721a and 721b projecting to the inside are provided respectively at lower end portions of the pressing portions 72a and 72b. In addition, the projected portions 721a and 721b are provided with inclined tapered surfaces 722a and 722b on the upper side.

The second member 7 is normally in the condition where the operating portion 71 is lifted (spaced) from the upper wall 613 by the biasing force of the leaf spring 65, as shown in FIG. 5. When the operating portion 71 is depressed by a finger, the second member 7 is displaced downwards against the biasing force of the leaf spring 65, and the lower surface of the operating portion 71 comes into contact with the upper wall 613, as shown in FIG. 6. In conjunction with such operations at the operating portion 71, the pressing portions 72a and 72b are each displaced between a first position shown in FIG. 5 and a second position shown in FIG. 6 which is deviated downwards from the first position.

As shown in FIG. 5, when the pressing portions 72a and 72b are in their first positions, i.e., in the condition where the operating portion 71 is not depressed, the projected portions 721a and 721b are located at the same location (height) as the projected portions 632a and 632b, and are pressing the projected portions 632a and 632b inwards. This results in that the engaging portions 63a and 63b are displaced inwards, and the projections 631a and 631b are inserted into the engaging recessed portions 471 of the racks 47a and 47b, respectively. Thus, in the condition shown in FIG. 5, the engaging portions 63a and 63b are in engagement with the racks 47a and 47b, whereby the stopper 5 is fixed to the pusher 4.

As shown in FIG. 6, when the pressing portions 72a and 72b are in their second positions, i.e., in the condition where the operating portion 71 is depressed, the projected portions 721a and 721b are located on the lower side relative to the projected portions 632a and 632b, so that the pressing on the projected portions 632a and 632b is released (canceled). This results in that the engaging portions 63a and 63b are displaced outwards by their own elasticity, and the projections 631a and 631b are retracted from the engaging recessed portions 471 of the racks 47a and 47b. Thus, in the condition shown in FIG. 6, fixation of the stopper 5 is released (canceled), and the stopper 5 can be slid (moved) relative to the pusher 4.

When the depression on the operating portion 71 is released starting from the condition of FIG. 6, the second member 7 is displaced upwards by the biasing force of the leaf spring 65, and the pressing portions 72a and 72b are returned to their first positions, resulting in the fixation condition shown in FIG. 5. In this instance, the projected portions 632a and 632b can be smoothly returned to the condition of FIG. 5 by being pressed by the projected portions 721a and 721b while sliding on the tapered surfaces 722a and 722b, respectively. Particularly in the configuration shown in the figures, the hemispherical shape of the projected portions 632a and 632b reduces the friction between the projected portions 632a, 632b and the tapered surfaces 722a, 722b, so that the returning action occurs more smoothly and securely.

As has been described above, in the syringe 1, the stopper 5 is slid on the pusher 4 by depressing the operating portion 71 with a finger, whereby the position of the stopper 5 can be regulated. In addition, when the finger is detached from the operating portion 71 to release (remove) the depression, the stopper 5 is fixed in situ relative to the pusher 4. With the position of the stopper 5 on the pusher 4 thus regulated, the insertion depth of the pusher 4 insertable into the outer tube 2 can be changed, so that the amount of the chemical 100 discharged can be set to a desired amount.

Namely, in this embodiment, the racks 47a, 47b, the engaging portions 63a, 63b, the leaf spring 65 and the pressing portions 72a, 72b constitute the fixing means for selecting and fixing the position of the stopper 5 on the pusher 4.

As shown in FIG. 1, the pusher 4 (leaf spring 44) is provided with graduations 48 corresponding to the amount of the liquid discharged from the syringe 1. As will be described later, by pushing in the pusher 4 under the condition where the position of the tip end face 66 of the stopper 5 (first member 6) is matched to the graduations 48, it is possible to discharge a desired amount of the chemical 100.

The graduations 48 correspond to the graduations 27 provided on the outer tube 2, and, in the configuration shown, the graduations 48 are formed at positions corresponding to discharge liquid amounts of 0 to 5 mL.

In addition, the pusher 4 is provided with a positioning means for positioning the stopper 5 to 0 (zero) of the graduations 48. In this embodiment, the positioning means is composed of the second flange 42. Specifically, a base end face 421 of the second flange 42 is at a position corresponding to 0 (zero) of the graduations 48. This ensures that positioning of the stopper 5 to 0 (zero) of the graduations 48 (zero point setting) can be easily achieved by moving the stopper 5 in the tip end direction until the tip end face 66 abuts on the base end face 421 of the flange 42. With the zero point setting, it is possible to set the amount of the chemical 100 discharged to a more accurate amount, as will be described later.

Incidentally, the positioning means is not limited to such a configuration as the flange 42, as long as the positioning means prevents the stopper 5 from moving further in the tip end direction. For example, a step formed at an edge portion of the plate piece 46 or the like may also be adopted as the positioning means.

The material for constituting the stopper 5 is not particularly limited. Examples of the constituent material of the outer tube 2 which are usable include not only various synthetic resin materials like those mentioned above as the constituent material of the outer tube 2 but also various metallic materials such as stainless steels, aluminum or aluminum alloys, titanium or titanium alloys, copper or copper alloys, etc.

Incidentally, the fixing means for the stopper 5 may be one in which engaging portions constituted of recessed portions provided in the stopper are engaged with engaging projected portions formed in the racks. In such a case, the shape of the engaging projected portions of the racks may be arbitrary; for example, a V shape, a U shape, a roughly angular U shape, a semicircular shape and the like may be adopted.

In addition, the biasing means for biasing the second member 7 (pressing portions 72a, 72b) is not limited to the leaf spring 65, and may be any one; for example, the biasing means may be composed of a separate member such as a coil spring.

Incidentally, while a pair of the racks 47a, 47b and a pair of the engaging portions 63a, 63b are provided in this embodiment, one rack and one engaging portion may be provided in the present invention; further, three or more racks and three or more engaging portions may be provided in the present invention.

Next, one example of the method of using the syringe 1 will be described. The method described below pertains to an exemplary case in which a double ended needled holder (not shown) including a bottomed tubular holder main body and a double ended needle (needle pipe) having sharp needle ends at both ends thereof is connected to the syringe 1, and the chemical 100 is mixedly injected into a bottle-shaped or bag-shaped injection vessel (not shown).

[1A] First, the stopper 5 is positioned to 0 (zero) of the graduations 48 (zero point setting). Specifically, while pressing the operating portion 71 with a finger, the stopper 5 is moved to a maximum degree toward the side of the tip end of the pusher 4, bringing the tip end face 66 of the stopper 5 into contact with the base end face 421 of the second flange 42. As has been described above, when the finger is detached from the operating portion 71, the stopper 5 is fixed in site on the pusher 4.

[2A] Next, deaeration of the outer tube 2 is conducted as follows. As shown in FIG. 1, the syringe 1 is charged with the chemical 100 in an amount slightly larger than a prescribed amount (5 mL, in the configuration shown in the figures). The holder main body of the double ended needled holder is fitted over the cap 29 of the syringe 1. This results in that one of the needle ends of the double ended needle pierces through the film 24, entering into the lumen 23 of the diameter-reduced portion 22. After the double ended needled holder is thus fitted, a finger is put on the finger receiving portion 401 of the pusher 4, and the pusher 4 is moved in the tip end direction relative to the outer tube 2 until the tip end face 66 of the stopper 5 abuts on the base end portion 28 of the outer tube 2. By this operation, the gasket 3 connected to the pusher 4 is slid in the outer tube 2 in the tip end direction, and a surplus amount of the chemical 100 and air in the outer tube 2 are discharged through the lumen 23 of the diameter-reduced portion 22 and the double ended needle.

Upon this operation, the amount of the chemical 100 in the outer tube 2 is equal to the prescribed amount. In other words, under this condition, the outer circumferential portion tip end (projected portion 33) of the gasket 3 is located at the position, corresponding to the prescribed amount (5 mL, in the configuration shown in the figures), in the graduations 27 on the outer tube 2.

[3A] Subsequently, the other end of the double ended needle of the double ended needled holder is caused to pierce through a plug body sealing a mouth portion of the injection vessel. In this condition, the inside of the outer tube 2 and the interior space of the injection vessel are communicated with each other through the double ended needle.

[4A] Next, while pressing the operating portion 71 with a finger, the stopper 5 is slid on the pusher 4 so as to position the tip end face 66 of the stopper 5 to a position, corresponding to the desired discharge amount, on the graduations 48. In the configuration shown in the figures, for example, where 1 mL of the chemical 100 is to be discharged, the tip end face 66 is positioned to "1" on the graduations 48. Where 3 mL of the chemical 100 is to be discharged, the tip end face 66 is positioned to "3" on the graduations 48.

[5A] Subsequently, a finger is put on the finger receiving portion 401, the pusher 4 is pushed in the tip end direction, and the pusher 4 is moved in the tip end direction relative to the outer tube 2 until the tip end face 66 of the stopper 5 abuts on the base end portion 28 of the outer tube 2. By this operation, the gasket 3 connected to the pusher 4 is slid in the outer tube 2 in the tip end direction, and the set amount of the chemical 100 is discharged from the outer tube 2 through the lumen 23 of the diameter-reduced portion 22 and the double ended needle, to be blended into the injection present in the injection vessel.

Thus, in the present invention, the depth of insertion of the pusher 4 into the outer tube 2 is restricted by the abutment of the stopper 5 on the outer tube 2; therefore, the pusher 4 is prevented from being pushed excessively or insufficiently, and the set amount of the chemical 100 can be discharged accurately. Therefore, a mistake such that the amount of the chemical 100 discharged is excessive or insufficient can be prevented from occurring.

In addition, in the syringe 1, the fixation of the stopper 5 can be released (canceled) and the position of the stopper 5 on the pusher 4 can be regulated, in a one-stroke operation of simply pressing the operating portion 71 with a finger. This ensures that the operation of setting the amount of the chemical 100 to be discharged can be performed extremely easily and swiftly.

Besides, when the depression on the operating portion 71 is released, the stopper 5 is automatically returned to the fixed state, so that the position of the stopper 5 once set is prevented from being deviated with the result of an error in the set discharge amount.

In addition, in the operation of discharging the chemical 100, the above-mentioned effect can be attained by the simple operation of only moving the pusher 4 in the tip end direction until the stopper 5 abuts on the outer tube 2, so that the operation of the pusher 4 does not need a subtle regulation of force, and the operation is easy to perform.

Incidentally, other than the above-described method of using the syringe 1, a method of using the syringe 1 in which a surplus amount of the chemical 100 is preliminarily discarded can also be adopted.

[1B] The case of using only 3 mL of the prescribed amount of 5 mL, in the configuration shown in the figures, will be described as an example. First, the tip end face 66 of the stopper 5 is adjusted to a position, corresponding to the surplus amount of the chemical 100, on the graduations 48. In this case, since the amount to be used is 3 mL against the prescribed amount of 5 mL and the surplus amount is therefore 2 mL, the tip end face 66 is adjusted to "2" on the graduations 48.

[2B] Next, the double ended needled holder is mounted to the cap 29 of the syringe 1 in the same manner as above, then a finger is put on the finger receiving portion 401 of the pusher 4, and the pusher 4 is moved in the tip end direction relative to the outer tube 2 until the tip end face 66 of the stopper 5 comes into contact with the base end portion 28 of the outer tube 2. By this operation, the gasket 3 connected to the pusher 4 is slid in the outer tube 2 in the tip end direction, and the surplus amount of the chemical 100 and air in the outer tube 2 are discharged through the lumen 23 of the diameter-reduced portion 22 and the double ended needle. As a result of the operation, deaeration is achieved, and 3 mL of the chemical 100 is left in the outer tube 2. In other words, under this condition, the outer circumferential portion tip end (projected portion 33) of the gasket 3 is located at "3" of the graduations 27 on the outer tube 2.

[3B] Subsequently, in the same manner as above, the other end of the double ended needle of the double ended needled holder is caused to pierce through the plug body sealing the mouth portion of an injection vessel, whereby the inside of the outer tube 2 and the interior space of the injection vessel are communicated with each other.

[4B] Next, while pressing the operating portion 71 with a finger, the stopper 5 is slid on the pusher 4, to a base end portion (on the base end side relative to "5" of the graduations 48, in the configuration shown in the figures) of the pusher 4.

[5B] Subsequently, a finger is put on the finger receiving portion 401, the pusher 4 is pressed, and the pusher 4 is moved in the tip end direction until the tip end face 36 of the gasket 3 comes into contact with (or into proximity to) the bottom portion 21 of the outer tube 2, thereby discharging substantially completely the chemical 100 remaining in the outer tube 2. By this operation, the desired amount (3 mL) of the chemical 100 can be blended into the injection in the injection vessel.

Incidentally, while the syringe 1 pre-filled with the liquid chemical 100 has been described in this embodiment, the chemical 100 in the present invention may be solid. In this case, the pusher 4 is pulled in the base end direction to suck in a liquid through the tip end opening of the diameter-reduced portion 22 into the inside of the outer tube 2, thereby dissolving the chemical 100 in the liquid, before use. In addition, the present invention is applicable not only to a pre-filled syringe such as the syringe 1 but also to an ordinary syringe in which a chemical or the like is not sealed.

Besides, while the operating portion 71 has been to be pressed with a finger in this embodiment, an operating portion which is subjected to a traction operation (pulling operation) or a nipping operation (pinching operation) with fingers so as to release the fixation of the stopper 5 may also be adopted in the present invention.

In addition, naturally, the method of using the syringe 1 is not limited to the one in which the double ended needled holder as above-described is used, but may be one in which, for example, a hub, connectors, tubes or the like (not shown) of the needle pipe is fitted over or mounted to the diameter-reduced portion 22.

Second Embodiment

Figure 7:
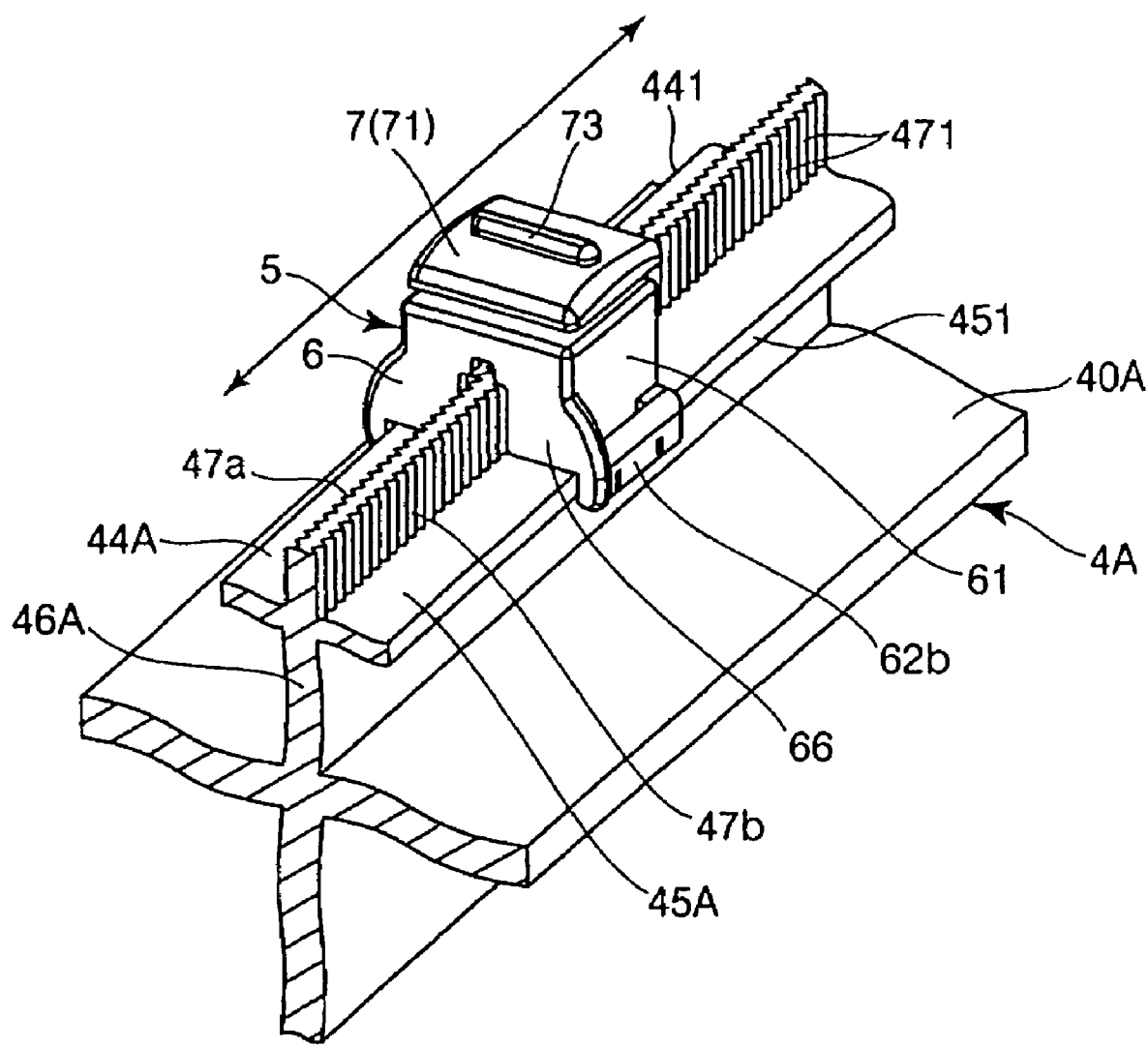
FIG. 7 is a perspective view of a main body portion of a pusher and a stopper in a second embodiment of the syringe according to the present invention.

FIG. 7 is a perspective view of a main body portion of a pusher and a stopper in a second embodiment of the syringe according to the present invention.

The second embodiment of the syringe according to the present invention will be described below referring to the drawing. In the following, description will be centered on the differences from the above-described embodiment, and description of the same items as above will be omitted.

A pusher 4A in this embodiment is one for use in a syringe which is larger in size (capacity) than the syringe 1 in the first embodiment. Namely, the pusher 4A is larger than the pusher 4 in the first embodiment.

A main body portion 40A of the pusher 4A has a shape such that plate pieces are intersected in a cross form. The main body portion 40A is provided with a stopper 5 the same with or similar to the above-mentioned. The width (maximum width) of the stopper 5 is smaller than the width (maximum width) of the main body portion 40A.

From both side surfaces of one plate piece 46A of the four plate pieces constituting the main body 40A, plate pieces 44A and 45A are projected. Namely, the plate pieces 44A and 45A are intersected with the plate piece 46A at right angles. Edge portions of the plate pieces 44A and 45A constitute rail portions 441 and 451 on which the stopper 5 is slid.

The plate piece 46A, located on the upper side relative to the plate pieces 44A and 45A in FIG. 7, is provided with racks 47a and 47b on both side surfaces thereof.

Thus, in this embodiment, the stopper 5 having a maximum width smaller than the maximum width of the main body portion 40A (pusher 4A) can be disposed and used. Therefore, for example, the stopper 5 having the same size and configuration as those in the first embodiment can be disposed and used for the pusher 4A larger in size than that in the first embodiment. Accordingly, in the case of applying the present invention to a large-sized syringe, a stopper 5 for a small-sized syringe can be used in common, so that it is unnecessary to design and produce a large-sized stopper and, therefore, to contrive a reduction in production cost. In addition, it is possible to contrive a reduction in weight of the syringe, as compared with the case of disposing a large-sized stopper; therefore, it is possible to preclude bad effects of an increase in weight, such as worsening of operationality.

Third Embodiment

Figure 8:
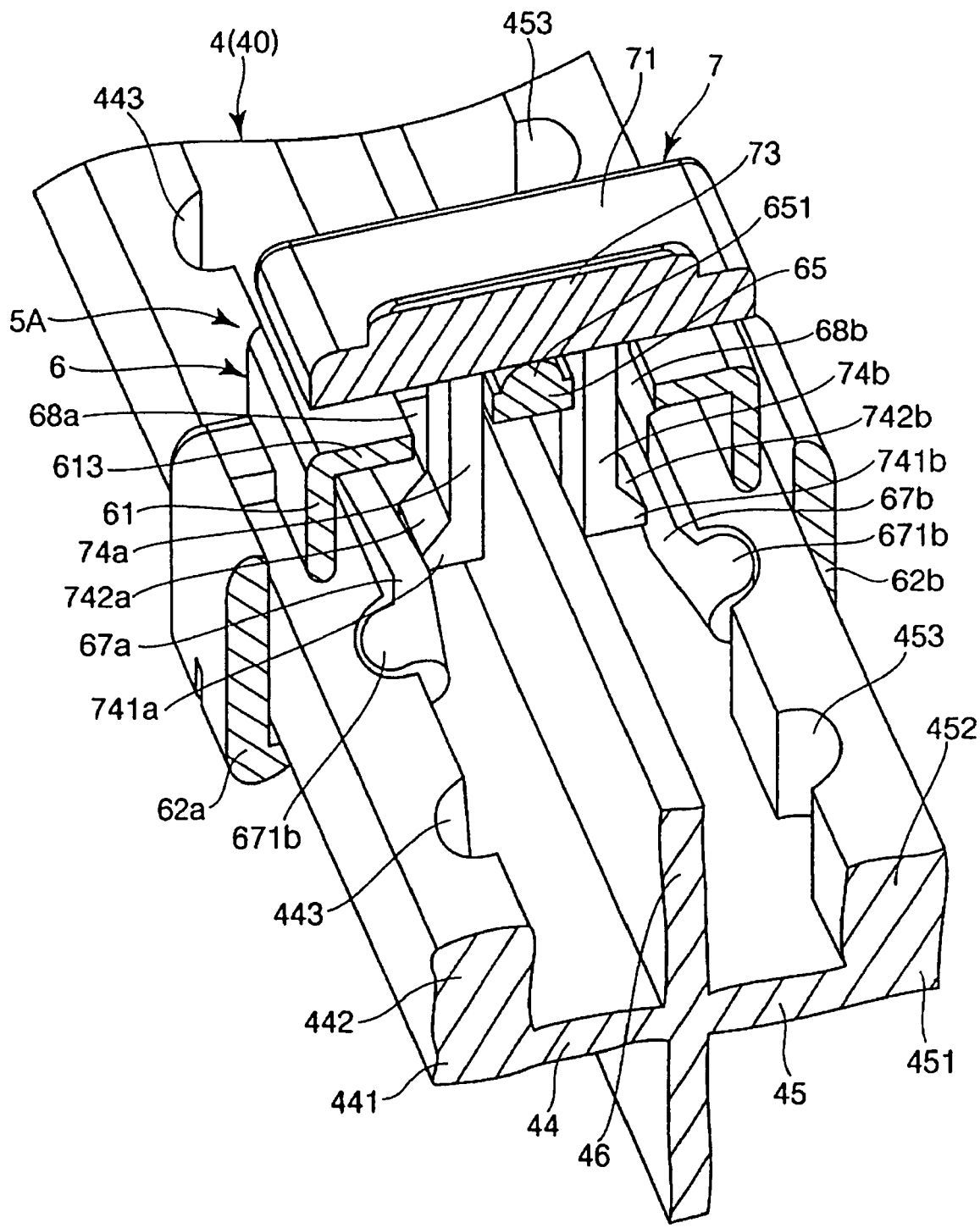
FIG. 8 is a partly sectional perspective view (in a state the stopper being fixed) showing a main body portion of a pusher and a stopper in a third embodiment of the syringe according to the present invention.
Figure 9:
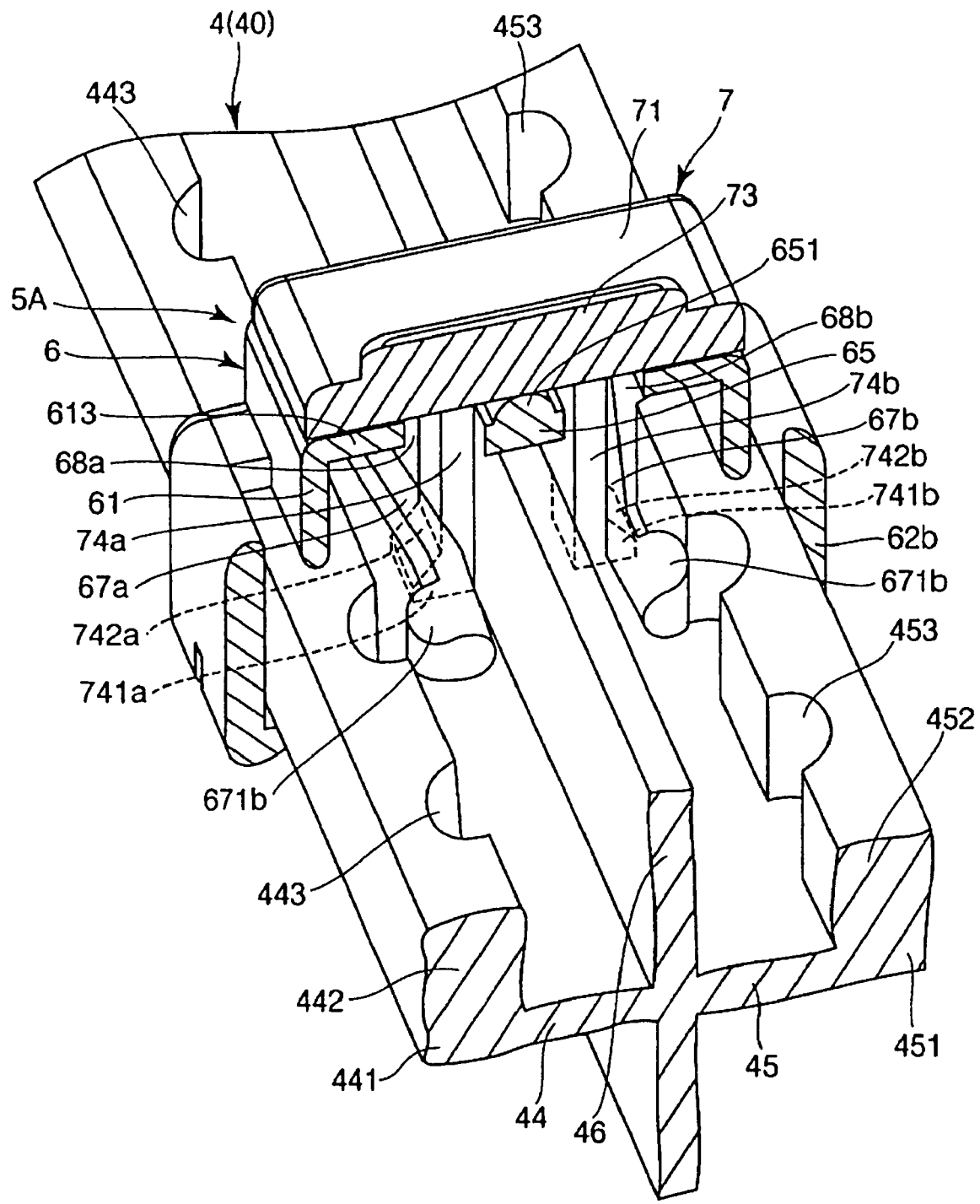
FIG. 9 is a partly sectional perspective view (in a state a fixation being released) showing the main body portion of the pusher and the stopper in the third embodiment of the syringe according to the present invention.

FIGS. 8 and 9 are partly sectional perspective views of a main body portion of a pusher and a stopper in a third embodiment of the syringe according to the present invention. Incidentally, for convenience of description, the side of the stopper in FIGS. 8 and 9 will be referred to as "upper", and the side of the main body portion of the pusher as "lower".

Now, the third embodiment of the syringe according to the present invention will be described below referring to these figures. In the following, description will be centered on differences from the above-described embodiments, and description of the same items as above will be omitted.

This embodiment is the same as the first embodiment, except for the configuration of the fixing means for fixing the stopper to the pusher.

In this embodiment, plate pieces 44 and 45 of the pusher 4 are provided at their edge portions with ribs extending in the longitudinal direction, and the ribs constitute racks 442 and 452, respectively.

Of the racks 442 and 452, the surfaces facing a plate piece 46 are provided with pluralities of engaging recessed portions 443 and 453 at a predetermined interval. In the configuration shown in the figures, the engaging recessed portions 443 and 453 are composed of roughly U-shaped grooves.

The stopper 5A is composed of a first member 6 and a second member 7.

From a base end wall 615 (see FIG. 4) of the first member 6, engaging portions 67a and 67b to be engaged with the racks 442 and 452 are extended in the shape of arms in the tip end direction. The engaging portion 67a is located between the rack 442 and the plate piece 46, and the engaging portion 67b is located between the rack 452 and the plate piece 46.

On tip end portions of the engaging portions 67a and 67b, projections 671a and 671b capable of being inserted into the engaging recessed portions 443 and 453 are formed to project outwards. The projections 671a and 671b are roughly U shaped (semicylindrically shaped).

An upper wall 613 of the first member 6 is provided with holes 68a and 68b on both sides of the leaf spring 65.

From the lower surface of an operating portion 71 of the second member 7, pressing portions 74a and 74b are projected in the form of arms. The second member 7 is disposed on the first member 6 in the condition where the pressing portions 74a and 74b are inserted in the holes 68a and 68b, respectively. In this mounted state, the pressing portions 74a and 74b, on the tip end side, are located on the inside of the engaging portions 67a and 67b.

At lower end portions of the pressing portions 74a and 74b, projected portions 741a and 741b are respectively formed to project outwards. In addition, the projected portions 741a and 741b are respectively provided with inclined tapered surfaces 742a and 742b on the upper side.

In this embodiment, the racks 442, 452, the engaging portions 67a, 67b, the leaf spring 65 and the pressing portions 74a, 74b constitute a fixing means for fixing the stopper 5A to the pusher 4.

Normally, the second member 7 is in the state of being lifted (spaced) from the upper wall 613 of the operating portion 71 by a biasing force of the leaf spring 65, as shown in FIG. 8. When the operating portion 71 is depressed with a finger, the second member 7 is displaced downwards against the biasing force of the leaf spring 65, and the lower surface of the operating portion 71 makes contact with the upper wall 613, as shown in FIG. 9.

In conjunction with such operations at the operating portion 71, the pressing portions 74a and 74b are each displaced between a first position shown in FIG. 8 and a second position shown in FIG. 9 which is deviated downwards from the first position.

When the pressing portions 74a and 74b are at their first positions as shown in FIG. 8, i.e., in the condition where the operating portion 71 is not depressed, the projected portions 741a and 741b are at the same positions (height) as the engaging portions 67a and 67b, pressing the engaging portions 67a and 67b outwards. As a result, the engaging portions 67a and 67b are respectively displaced outwards, and the projections 671a and 671b are inserted in the engaging recessed portions 443 and 453 of the racks 442 and 452, respectively. Thus, in the condition shown in FIG. 8, the engaging portions 67a and 67b are engaged with the racks 442 and 452, whereby the stopper 5A is fixed to the pusher 4.

When the pressing portions 74a and 74b are at their second positions as shown in FIG. 9, i.e., in the condition where the operating portion 71 is depressed, the projected portions 741a and 741b are located on the lower side relative to the engaging portions 67a and 67b, so that the pressing on the engaging portions 67a and 67b is released. As a result, the engaging portions 67a and 67b are displaced inwards by their own elasticity, and the projections 671a and 671b are retracted from the engaging recessed portions 443 and 453 of the racks 442 and 452. Thus, in the condition shown in FIG. 9, fixation of the stopper 5A is released (canceled), and the stopper 5A can be slid (moved) relative to the pusher 4.

When the depression on the operating portion 71 is released starting from the condition shown in FIG. 9, the second member 7 is displaced upwards by the biasing force of the leaf spring 65, and the pressing portions 74a and 74b are returned to their first positions, whereby the fixed state shown in FIG. 8 is retained. In this instance, the engaging portions 67a and 67b can be smoothly returned to the condition shown in FIG. 8, by being pressed against the projected portions 741a and 741b while sliding on the tapered surface 742a and 742b.

Thus, in this embodiment, like in the first embodiment, the stopper 5A can be slid on the pusher 4 and the position of the stopper 5A can be easily regulated, by depressing the operating portion 71 with a finger.

Fourth Embodiment

Figure 10:
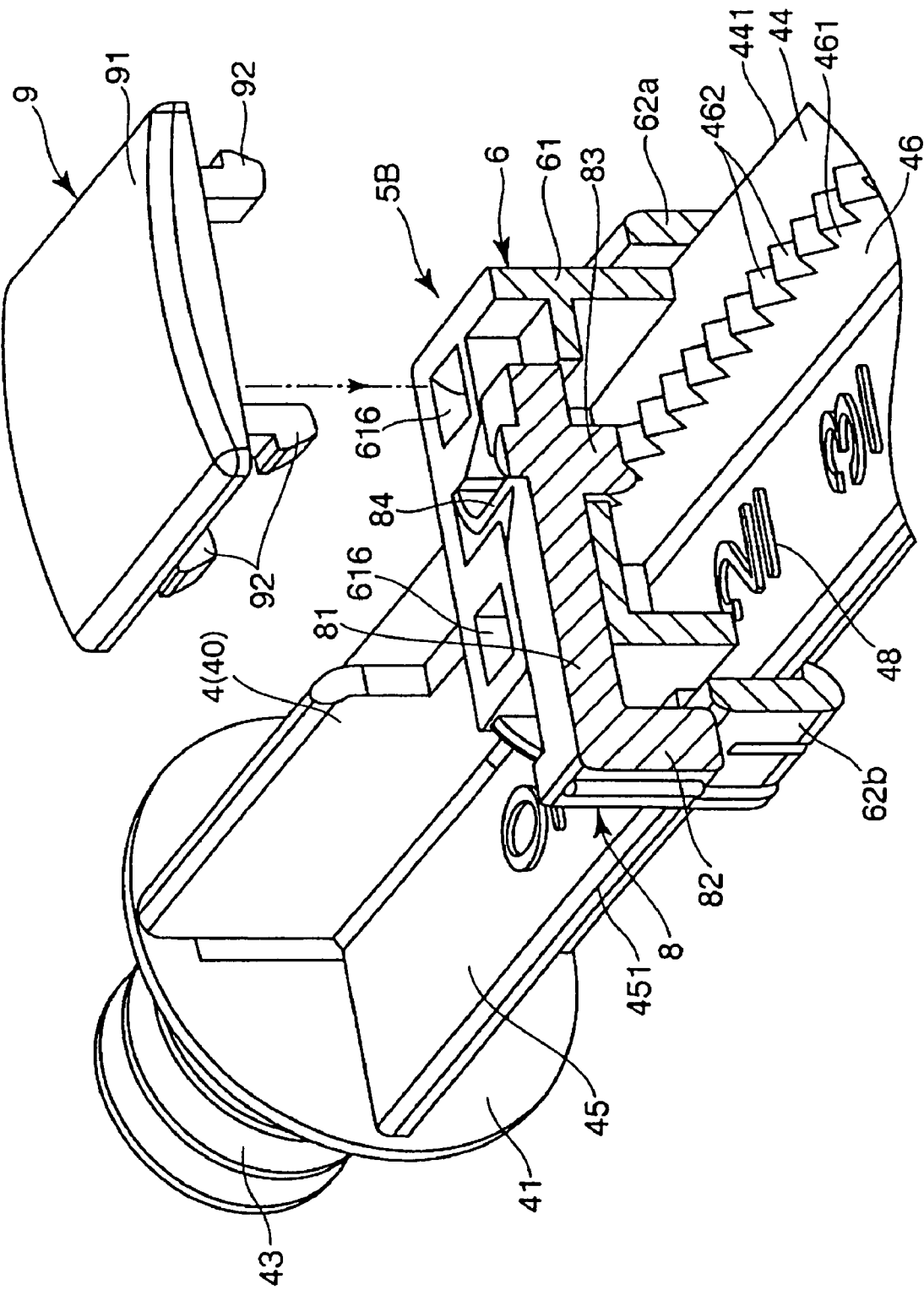
FIG. 10 is a partly sectional perspective view (in a state the stopper being fixed) showing a pusher and a stopper in a fourth embodiment of the syringe according to the present invention.
Figure 11:
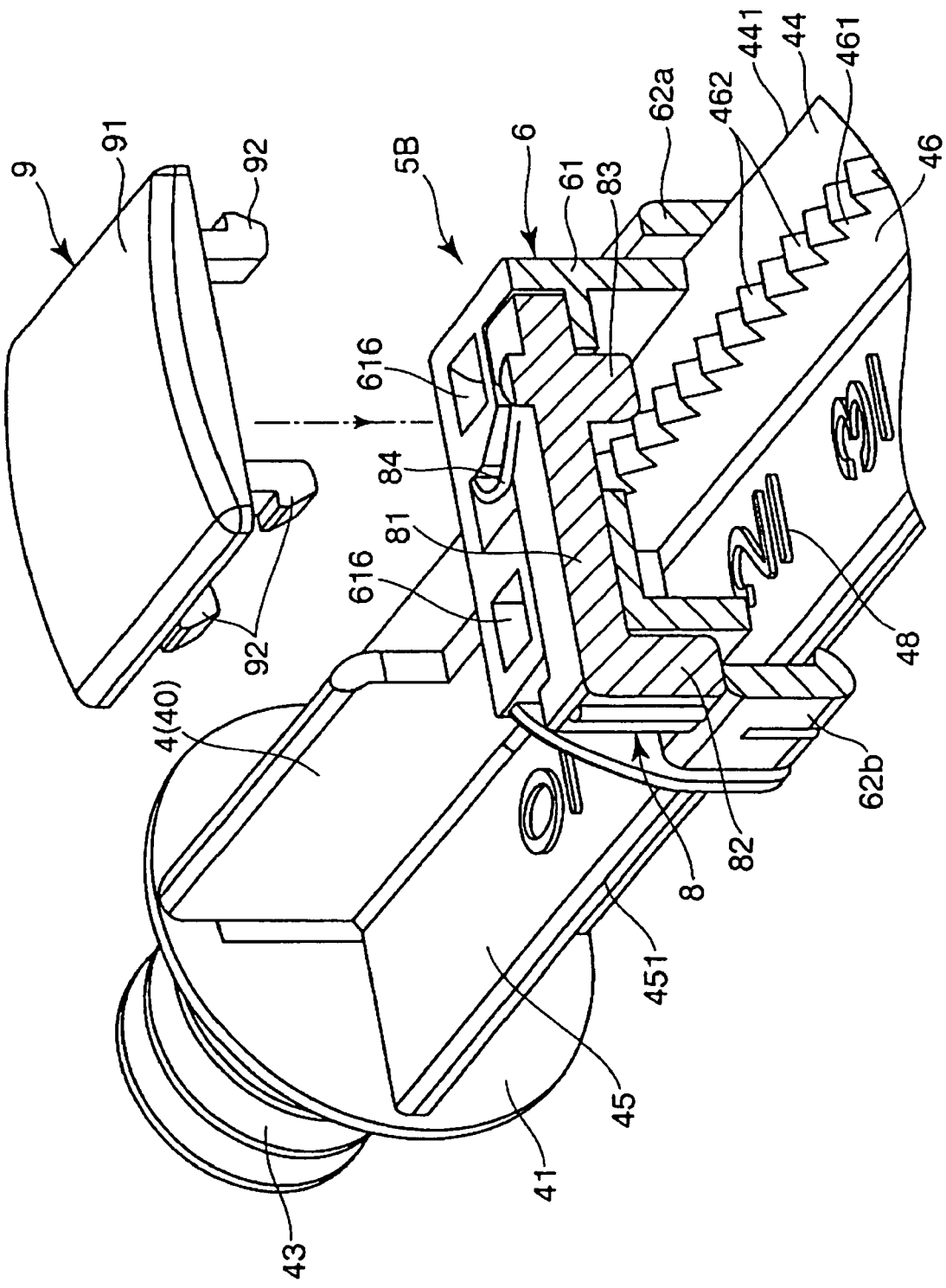
FIG. 11 is a partly sectional perspective view (in a state a fixation being released) showing the pusher and the stopper in the fourth embodiment of the syringe according to the present invention.

FIGS. 10 and 11 are partly sectional perspective views of a pusher and a stopper in a fourth embodiment of the syringe according to the present invention. Incidentally, for convenience of description, the side of a third member of the stopper in FIGS. 10 and 11 will be referred to as "upper", and the side of the pusher as "lower".

Now, the fourth embodiment of the syringe according to the present invention will be described below referring these figures. In the following, description will be centered on differences from the above-mentioned embodiments, and description of the same items as above will be omitted.

This embodiment is the same as the first embodiment, except for the configuration of the fixing means for fixing the stopper to the pusher.

In this embodiment, a plate piece 46 of the pusher 4 is provided at its edge portion with a plurality of engaging recessed portions 462 at a predetermined interval along the longitudinal direction, to constitute a rack 461. The engaging recessed portions 462 are composed of roughly V-shaped notches (grooves), so that the rack 461 is serrate.

The stopper 5B is composed of a first member 6, a second member 8, and a third member 9. In FIGS. 10 and 11, the first member 6 and the second member 8 are shown in the state of being cut in the direction orthogonal to the longitudinal direction of the pusher 4, at the center in the longitudinal direction.

The internal structure of the stopper 5B is symmetrical on the tip end side and the base end side. Namely, while the first member 6 and the second member 8 are shown only on the tip end side in FIGS. 10 and 11, the members on the base end side are symmetrical with the members on the tip end side.

The second member 8 includes a plate-like (rod-like) main body portion 81, which is disposed in the state of being inserted into a casing 61 of the first member 6 from a lateral side. The main body portion 81 is provided at its end portion with an operating portion 82 which functions as a pushbutton. Namely, the operating portion 82 is provided on a lateral side of the stopper 5B.

The main body portion 81 is provided with a pair of leaf springs 84, 84 projecting to the tip end side and to the base end side, respectively. While only the leaf spring on the tip end side is shown in FIGS. 10 and 11, the same leaf spring is provided also on the base end side. The leaf springs 84 are formed integrally with the main body portion 81. Tip end portions of the leaf springs 84 are each in contact with an inside wall of the casing 61.

In addition, the main body portion 81 is provided with an engaging portion (projection) 83 capable of engagement with the rack 461, the engaging portion 83 formed to project downwards. The engaging portion 83 is edge shaped (V-shaped) in correspondence with the engaging recessed portions 462.

The third member 9 constitutes a cover body for the first member 6, and includes a roughly plate-like cover portion 91, and a plurality of (four, in the configuration shown in the figures) claw portions 92 projected from the lower surface of the cover portion 91. The first member 6 (casing 61) is provided with holes 616 respectively at positions corresponding to the claw portions 92, and the third member 9 is mounted to the first member 6 by inserting and fitting the claw portions 92 into the holes 616. Incidentally, while only two holes 616 on the tip end side are shown in FIGS. 10 and 11, the first member 6 is provided with two holes 616 also on the base end side. With the third member 9 mounted to the first member 6, the second member 8 is prevented from slipping off from the first member 6.

In this embodiment, the rack 461, the engaging portion 83 and the leaf springs 84 constitute the fixing means for fixing the stopper 5B to the pusher 4.

When the operating portion 82 is not depressed, as shown in FIG. 10, the left side of the main body portion 81 in the figure is in the state of being projected from the casing 61 by a biasing force of the leaf spring 84. In this condition, the engaging portion 83 is located in a position where it is inserted in the engaging recessed portion 462 of the rack 461, whereby the stopper 5B is fixed to the pusher 4.

When the operating portion 82 is pressed rightwards in the figure starting from this condition, the leaf spring 84 is deflected rightwards and the main body portion 81 is moved so as to sink into the inside of the casing 61, as shown in FIG. 11. By this movement of the main body portion 81, the engaging portion 83 is retracted to a lateral side of the rack 461. As a result, in the condition shown in FIG. 11, the fixation of the stopper 5B is released (canceled), so that the stopper 5B can be slid (moved) relative to the pusher 4.

When the depression on the operating portion 82 is released (canceled) starting from the condition shown in FIG. 11, the biasing force of the leaf spring 84 displaces the second member 8 (main body portion 81) leftwards, whereby the fixed state shown in FIG. 10 is retained.

Thus, in this embodiment, like in the first embodiment, the stopper 5B can be slid on the pusher 4 in the longitudinal direction of the pusher 4 and the position of the stopper 5B can be easily regulated, by depressing the operating portion 82 with a finger. In this case, since the operating portion 82 is provided at the lateral side of the stopper 5B in this embodiment, the operating portion 82 can be depressed by pinching the stopper 5B with two fingers from both sides. This ensures that, by sliding the stopper 5B while holding (pinching) the stopper 5B between two fingers, the position of the stopper 5B on the pusher 4 can be regulated, and the operation can be performed more easily.

Fifth Embodiment

Figure 12:
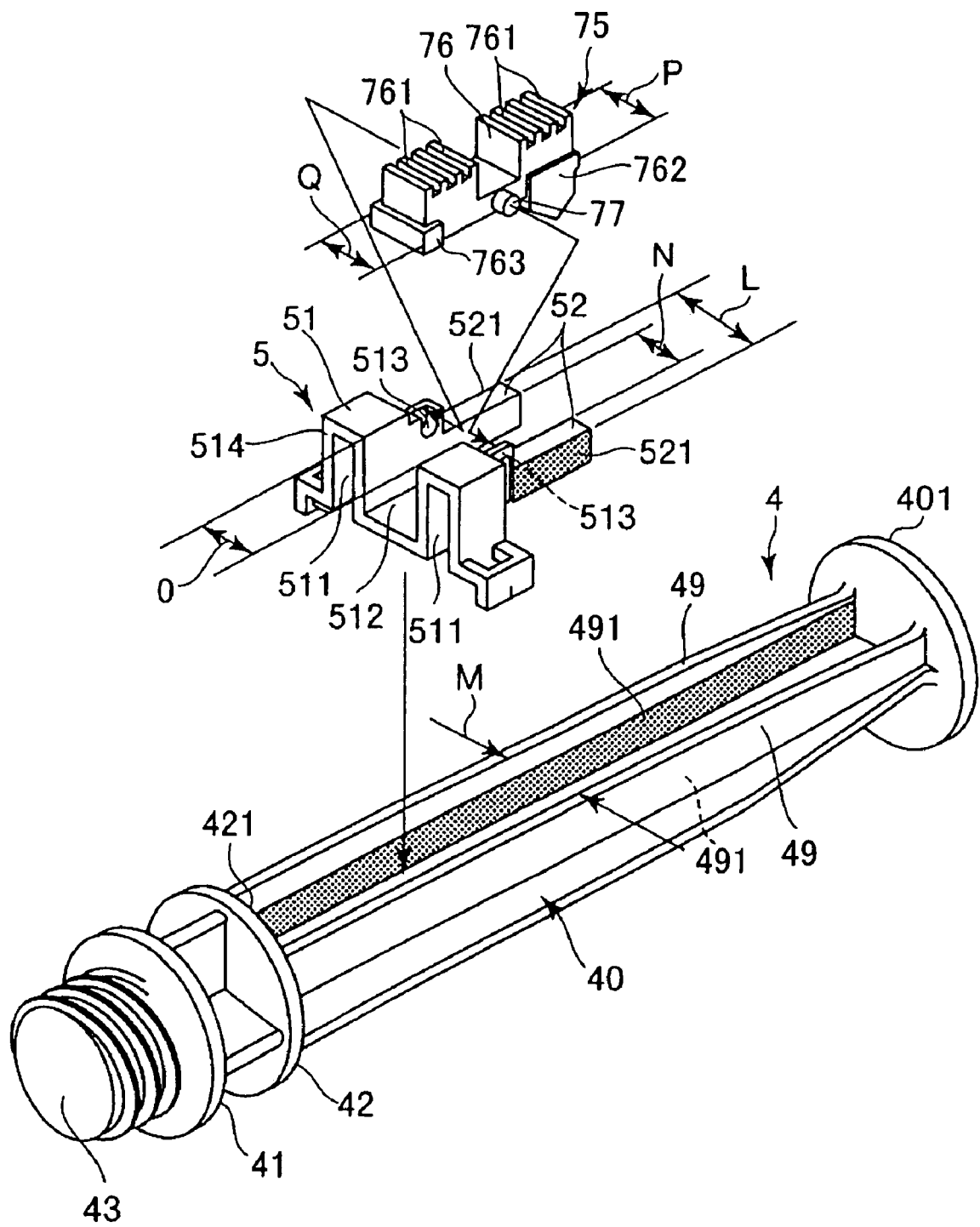
FIG. 12 is an exploded perspective view of a pusher portion in a fifth embodiment of the syringe according to the present invention.

FIG. 12 is an exploded perspective view of a pusher portion in a fifth embodiment of the syringe according to the present invention, and FIG. 13 shows perspective views illustrating the operating conditions of a stopper attached to the pusher portion shown in FIG. 12. Incidentally, for convenience of description, the side of a head (connection portion) of the pusher in FIGS. 12 and 13 will be referred to as "tip end", and the side of a flange-formed finger receiving portion as "base end".

Now, the fifth embodiment of the syringe according to the present invention will be described below. In the following, description will be centered on differences from the above-described embodiments, and description of the same items as above will be omitted.

In FIG. 12, the pusher 4 includes a main body portion 40 having the shape of a single plate piece extending in the longitudinal direction, instead of a main body portion having such a shape that plate pieces are intersected in a cross form. On the base end side of the main body portion 40, i.e., between a second flange 421 and a flange-formed finger receiving portion 401, a pair of rail portions (ribs) 49, 49 are formed integrally with the main body portion 40 along the longitudinal direction of the main body portion 40. The rail portion 49, 49 are provided to be substantially parallel to each other, and guide the stopper 5 which will be described later.

As shown in FIG. 12, the stopper 5 includes a stopper main body 51, and a brake portion 52. The stopper main body 51 and the brake portion 52 are each designed to be substantially symmetrical on the left and right sides.

The stopper main body 51 is provided with a pair of grooves (recessed portions) 511, 511 opening downwards, and the rail portions 49, 49 are inserted in the grooves 511, 511. By a movement of the stopper main body 51 along the rail portions 49, 49, the stopper 5 is moved along the longitudinal direction of the pusher 4.

In addition, the stopper main body 51 is provided at its central portion (between the grooves 511, 511) with a groove (recessed portion) 512 opening upwards. A fitting portion 763 formed at a lower portion of the tip end of an operating member 75 which will be described later is fitted in the groove 512.

The stopper main body 51 is provided with a pair of bearings 513, 513 on the base end side. An end portion of a rotary shaft 77 of an operating member 75 which will be described later is inserted in and rotatably fixed in each of the bearings 513.

The stopper main body 51 is provided at its base end with a pair of flat plate form brake portions 52, 52 which project in the base end direction and are substantially parallel to each other. Each of the brake portions 52 is formed integral with the stopper main body 51, and is elastically deformed, with its tip end as a fixed end and with its base end as a movable end.

In the condition where the stopper 5 is attached to the main body portion 40 of the pusher 4, the brake portions 52 are located on the inside of the rail portions 49, 49, respectively. With each brake portion 52 (a portion of the stopper 5) pressed against each rail portion 49, the stopper 5 is fixed relative to the pusher 4. On the other hand, with each brake portion 52 spaced from each rail portion 49, the fixation of the stopper 5 relative to the pusher 4 is released (canceled). Incidentally, the distance between outer surfaces 521 of the brake portions 52 (length L, in FIG. 12) is nearly equal to or slightly smaller than the distance between inner surfaces 491 of the rail portions 49 (length M, in FIG. 12). Therefore, in the condition where the fixation of the stopper 5 to the pusher 4 is released, the stopper 5 can be smoothly moved along the longitudinal direction of the pusher 4.

Thus, in this embodiment, the inner surfaces 491 of the rail portions 49 and the outer surfaces 521 of the brake portions 52 constitute contact surfaces which are pressed against each other. Incidentally, since the pair of rail portions 49 are substantially parallel to each other as above-described, the pair of the contact surfaces of the pusher 4 are substantially parallel to each other and face each other.

In this embodiment, the outer surfaces 521 of the brake portions 52 and the inner surfaces 491 of the rail portions 49 are both constituted of rough surfaces. This makes it possible to fix the stopper 5 relative to the pusher 4 more securely.

In the first to fourth embodiments of the syringe according to the present invention in which the stopper is fixed relative to the pusher by the engagement between the engaging recessed portions (or engaging projected portions) provided in the rack(s) formed on the main body portion of the pusher and the engaging projected portion(s) (engaging recessed portion(s)) provided in the stopper as above-described, the minimum of the amount of the chemical discharged from the syringe (dose) is limited by the interval (pitch) of the engaging recessed portions (or engaging projected portions). On the other hand, the configuration according to this embodiment is advantageous in that the minimum of the amount of the chemical discharged from the syringe 1 can be set to be smaller, for example, it is possible to set the dose of the chemical more finely.

Incidentally, only one of the outer surface 521 of the brake portion 52 and the inner surface 491 of the rail portion 49 (namely, the contact surfaces of the stopper 5 and the pusher 4) may be constituted of a rough surface. In addition, either one or both of the outer surface 521 of the brake portion 52 and the inner surface 491 of the rail portion 49 may be formed of a material having a high frictional resistance (e.g., an elastic material such as various rubbers, various thermoplastic elastomers, etc.).

The stopper 5 is provided with an operating member 75 for fixing the stopper 5 relative to the pusher 4, the operating member 75 being so provided as to be turnable (displaceable).

The operating member 75 includes a main body portion 76, and rotary shafts 77, 77 projected laterally from the main body portion 76. The rotary shafts 77, 77 are inserted in bearings 513, 513 provided on the stopper main body 51, whereby the operating member 75 is turnable relative to the stopper main body 51.

The main body portion 76 is a portion to be depressed by a finger, and functions as a pushbutton. The main body portion 76 is provided on its upper surface with a plurality of ribs 761 showing an anti-slipping function at the time of depressing the operating member 75 (main body portion 76) with a finger.

A wedge portion (fitting portion) 762 projecting downwards is provided at a base end side lower portion of the main body portion 76, integrally with the main body portion 76. On the other hand, a fitting portion 763 projecting in the tip end direction is provided at a tip end side lower portion of the main body portion 76, integrally with the main body portion 76.

Figure 13A:
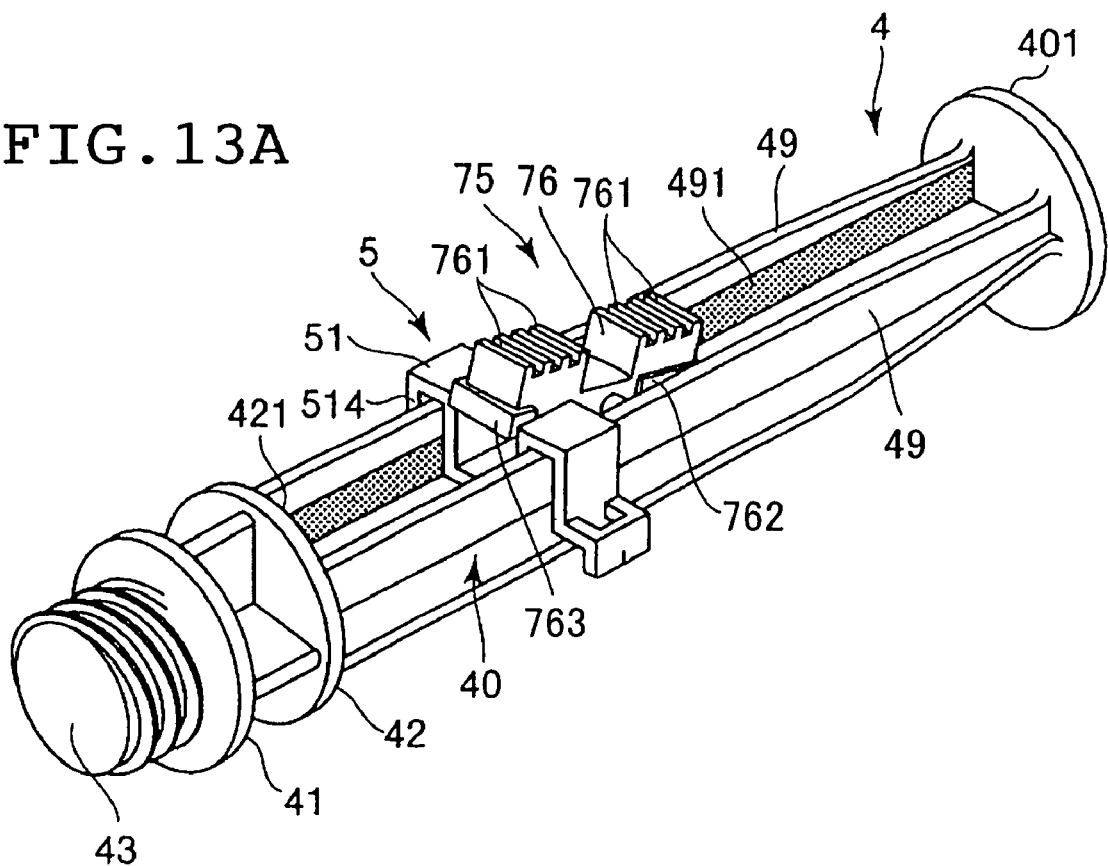
FIGS. 13A-13B shows perspective views illustrating the operating conditions of a stopper attached to the pusher portion shown in FIG. 12.

The width of the wedge portion 762 (length P, in FIG. 12) is set to be slightly larger than the interval between the inner surfaces 521 of the brake portions 52 (length N, in FIG. 12). Therefore, when the base end side of the operating member 75 (main body portion 76) is pressed toward the pusher 4, the operating member 75 is turned relative to the stopper 5 with the rotary shaft 77 as a center and the wedge portion 762 is displaced downwards, as shown in FIG. 13A. Then, the wedge portion 762 (a portion of the operating member 75) is inserted (fitted) between the brake portions 52, 52, pressing wider the brake portions 52, 52 in the directions for spacing away from each other. As a result, each brake portion 52 is clamped between the wedge portion 762 (a portion of the operating member 75) and the rail portion 49 (pusher 4) and is pressed against the pusher 4, whereby the stopper 5 is fixed relative to the pusher 4.

Figure 13B:
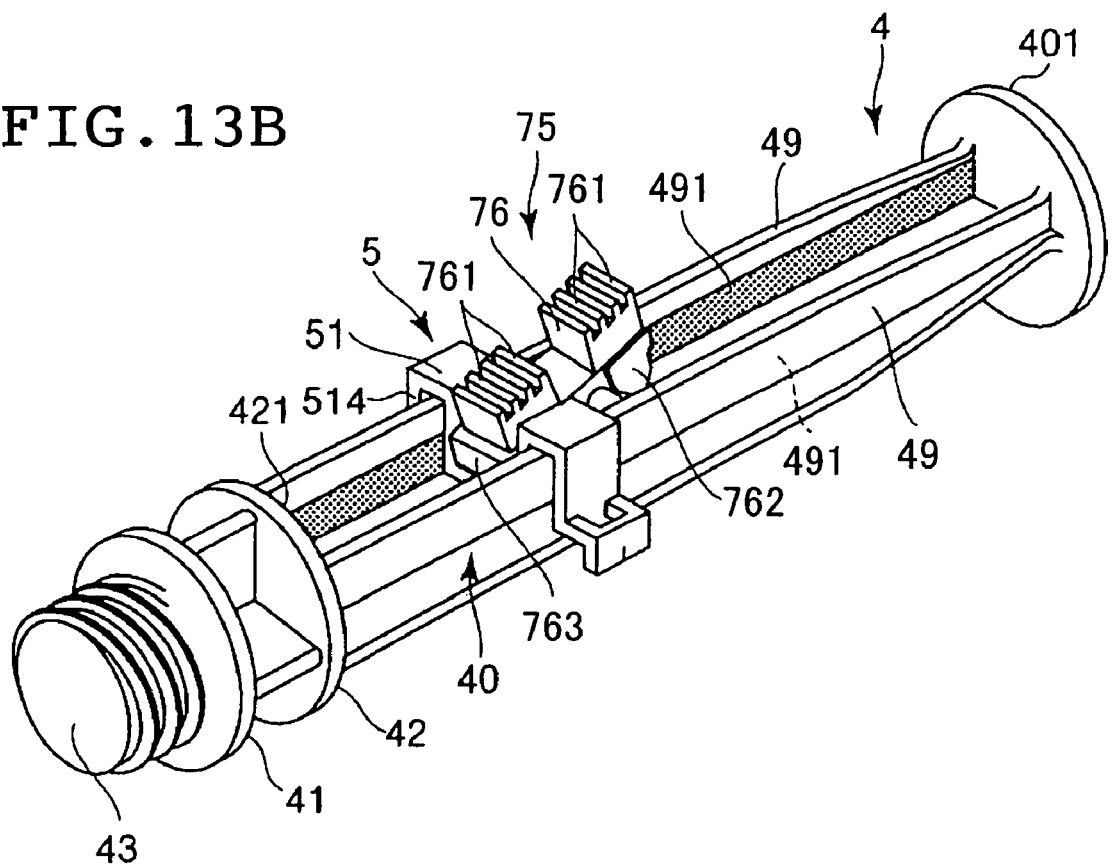

On the other hand, when the tip end side of the main body portion 76 of the operating member 75 is pressed toward the pusher 4 starting from this condition, the operating member 75 is turned relative to the stopper 5 with the rotary shaft 77 as a center and the wedge portion 762 is displaced upwards, as shown in FIG. 13B. As a result, the wedge portion 762 is released from between the brake portions 52, 52, and the fixation of the stopper 5 relative to the pusher 4 is released (canceled), so that the stopper 5 is slidable (movable) relative to the pusher 4.

In addition, the width of the fitting portion 763 (length Q, in FIG. 12) is set to be larger than the width of the groove 512 in the stopper main body 51 (length O, in FIG. 12), so that when the fitting portion 763 is fitted into the groove 512 of the stopper main body 51, the operating member 75 is fixed relative to the stopper main body 51 (see FIG. 13B). Therefore, during the operation of moving the stopper 5 in the longitudinal direction of the pusher 4, the operating member 75 can be prevented from moving (turning) to interfere with the operation.

As has been described above, in the syringe 1 according to this embodiment, by depressing the operating member 75 (main body portion 76) with a finger, it is possible to fix the stopper 5 to the pusher 4 and release the fixation, to slide the stopper 5 on the pusher, and to regulate the position of the stopper 5 to a desired position. By regulating the position of the stopper 5 on the pusher 4 in this manner, it is possible to change the depth of possible insertion of the pusher 4 into the outer tube 2 and, therefore, to set the amount of the chemical 100 discharged to a desired amount. Since the pusher 4 (main body portion 40) is provided with the graduations 48 corresponding to the amount of the chemical discharged from the syringe 1 as has been described in the first embodiment of the syringe, the desired amount of the chemical 100 can be discharged, by pushing in the pusher 4 in the condition where the position of a tip end face 514 of the stopper 5 (stopper main body 51) is regulated to the graduations 48.

Besides, since the pusher 4 is provided with the positioning means (second flange 42) for positioning the stopper 5 to 0 (zero) of the graduations 48, the stopper 5 can be easily positioned to 0 (zero) of the graduations (zero point setting), by moving the stopper 5 in the tip end direction until the tip end face 514 of the stopper 5 abuts on the base end face 421 of the second flange 42.

Sixth Embodiment

Figure 14:
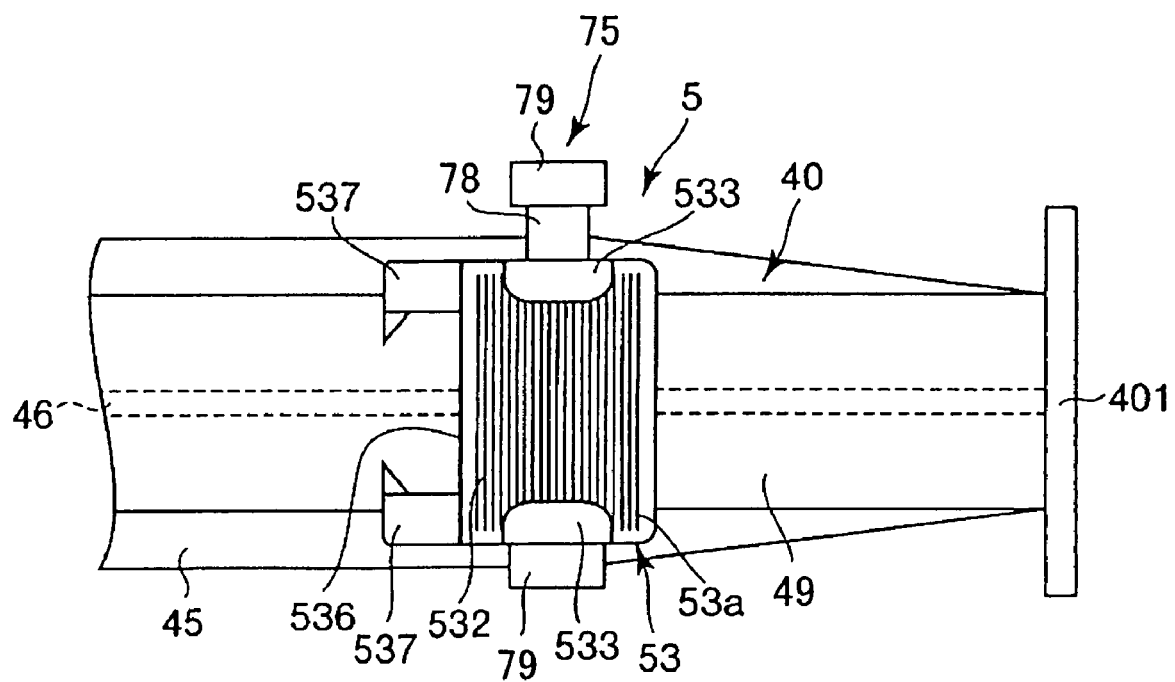
FIG. 14 is a plan view showing a main body portion of a pusher and a stopper in a sixth embodiment of the syringe according to the present invention.
Figure 16A:
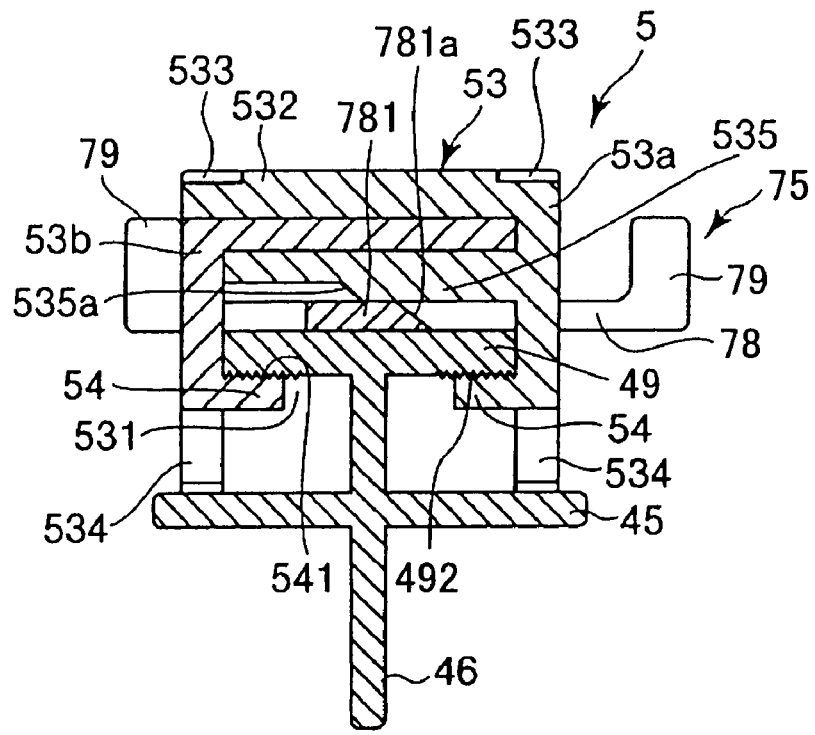
FIG. 16A-16B shows sectional views along line A-A of FIG. 15.
Figure 16B:
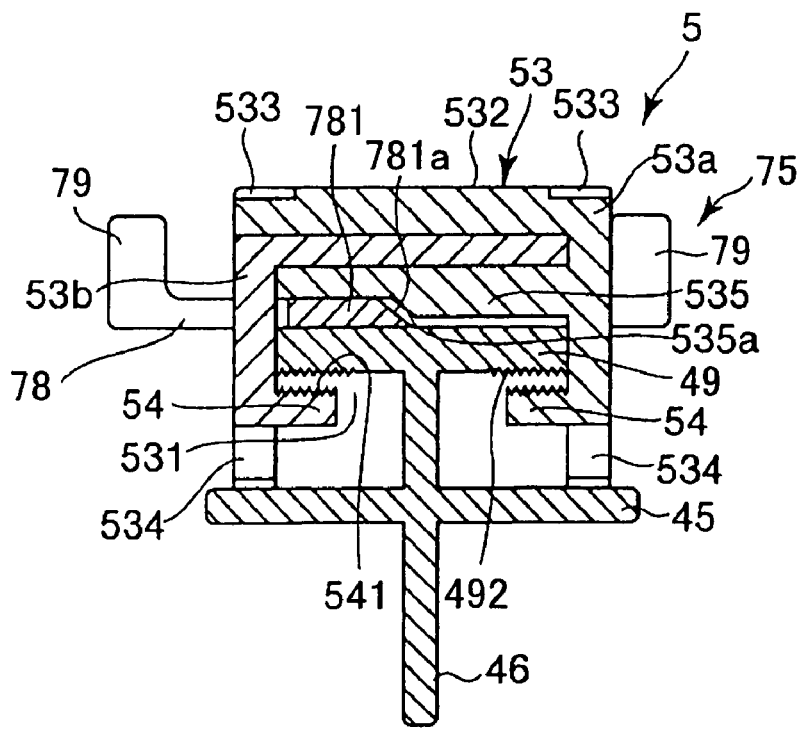
Figure 17A:
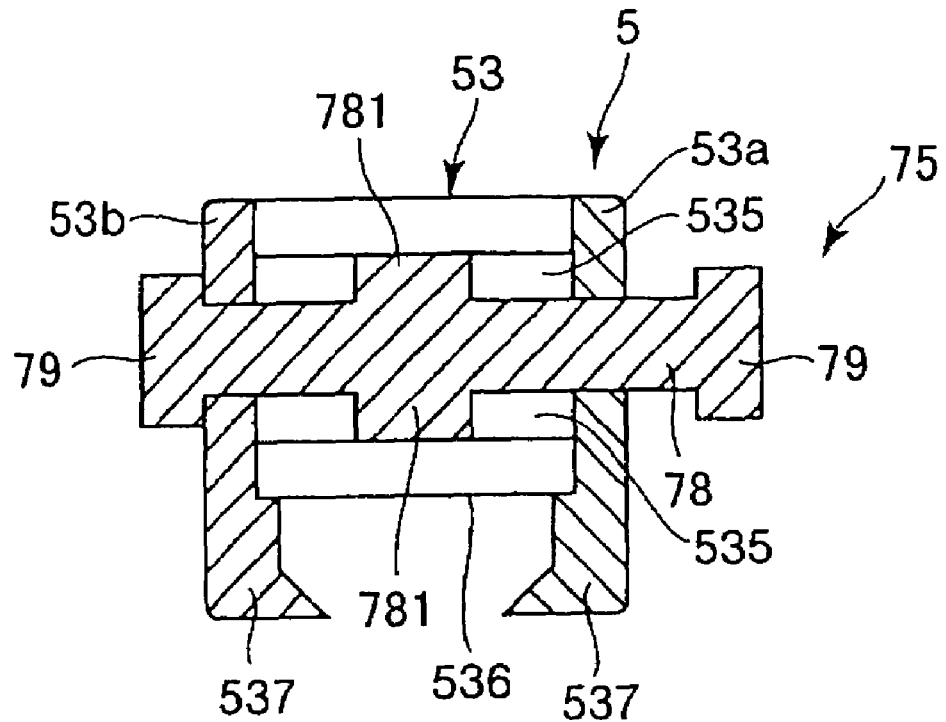
FIG. 17A-17B shows sectional views along line B-B of FIG. 15.
Figure 17B:
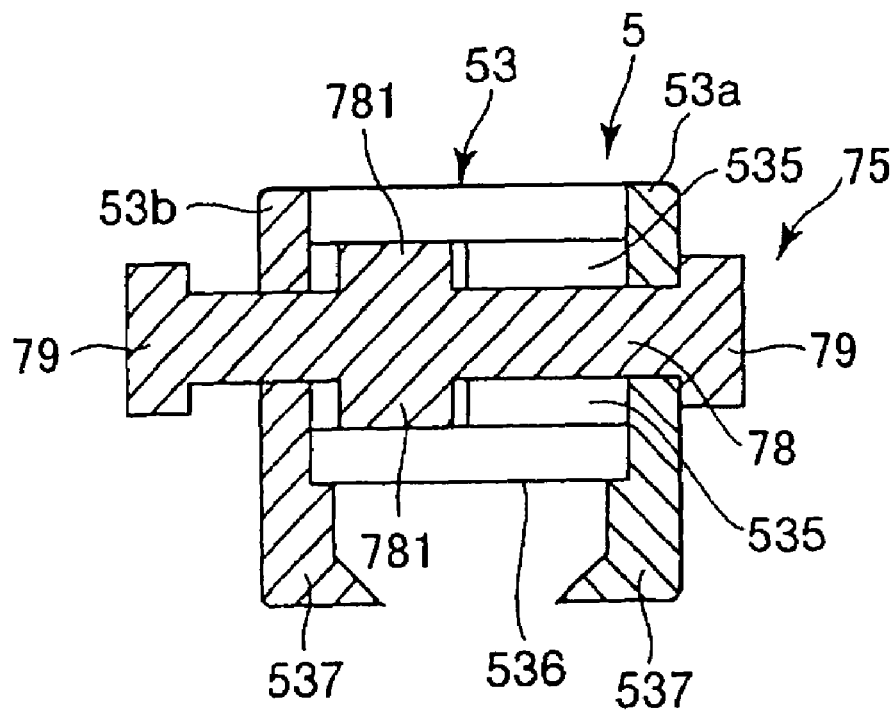

FIG. 14 is a plan view of a main body portion of a pusher and a stopper in a sixth embodiment of the syringe according to the present invention, FIG. 15 shows partly sectional side views illustrating the operating conditions of the stopper shown in FIG. 14, FIG. 16 shows sectional views along line A-A of FIG. 15, and FIG. 17 shows sectional views along line B-B of FIG. 15. Incidentally, for convenience of description, the side of a finger receiving portion of the pusher in FIGS. 14 and 15 will be referred to as "base end", the opposite side as "tip end", the viewer's side of the sheet of FIG. 16 will be referred to as "tip end", and the opposite side (the depth side) of the sheet as "base end", the lower side in FIG. 17 will be referred to as "tip end", and the upper side as "base end".

Now, the syringe according to the sixth embodiment will be described below. In the following, description will be centered on differences from the fifth embodiment, and description of the same items as above will be omitted.

The sixth embodiment is the same as the fifth embodiment, except for the configurations of the pusher, the stopper, and the operating member.

The pusher 4 in the sixth embodiment includes a main body portion 40 which has a shape such that two plate pieces 45 and 46 are intersected in a cross form.

At an upper edge portion of the plate piece 46, a plate piece form rail portion 49 is provided substantially in parallel to the plate piece 45. The rail portion 49 is formed integral with the pusher 4.

As shown in FIG. 16, the stopper 5 includes a stopper main body 53 composed of two members 53a, 53b, and a brake portion 54.

The stopper main body 53 is provided with a groove (recessed portion) 531 opening downwards. The rail portion 49 is inserted in the groove 531. With the stopper main body 53 moved along the rail portion 49, the stopper 5 is moved in the longitudinal direction of the pusher 4.

The stopper main body 53 is provided on its upper surface with a plurality of ribs 532 showing an anti-slipping function at the time of sliding the stopper 5 (stopper main body 53) with a finger.

These ribs 532 are provided with a pair of recessed portions 533 at both side portions thereof. Each recessed portion 533 is for securing an area for printing or labeling as an indication for easy discrimination between the condition where the stopper 5 is fixed and the condition where the fixation is released (canceled). Besides, the recessed portion 533 may have a surface projected or recessed in the shape of characters or symbols, or may have a surface decorated by printing or the like.

Four circular arc-shaped leg portions 534 are provided at lower portions of the stopper main body 53. Each leg portion 534 is elastically deformable. Provision of the leg portions 534 ensures that, at the time of moving the stopper 5 relative to the pusher 4, the pusher 5 can be prevented from chattering relative to the pusher 4, and the operation can be performed more securely.

At lower portions of the stopper main body 53, a pair of flat plate-like brake portions 54, 54 projecting inwards are provided substantially in parallel. Each brake portion 54 is formed integral with the stopper main body 53 (53a or 53b). In this configuration, the stopper 5 is provided so as to cover the rail portion 49 (see FIG. 16).

Figure 15A:
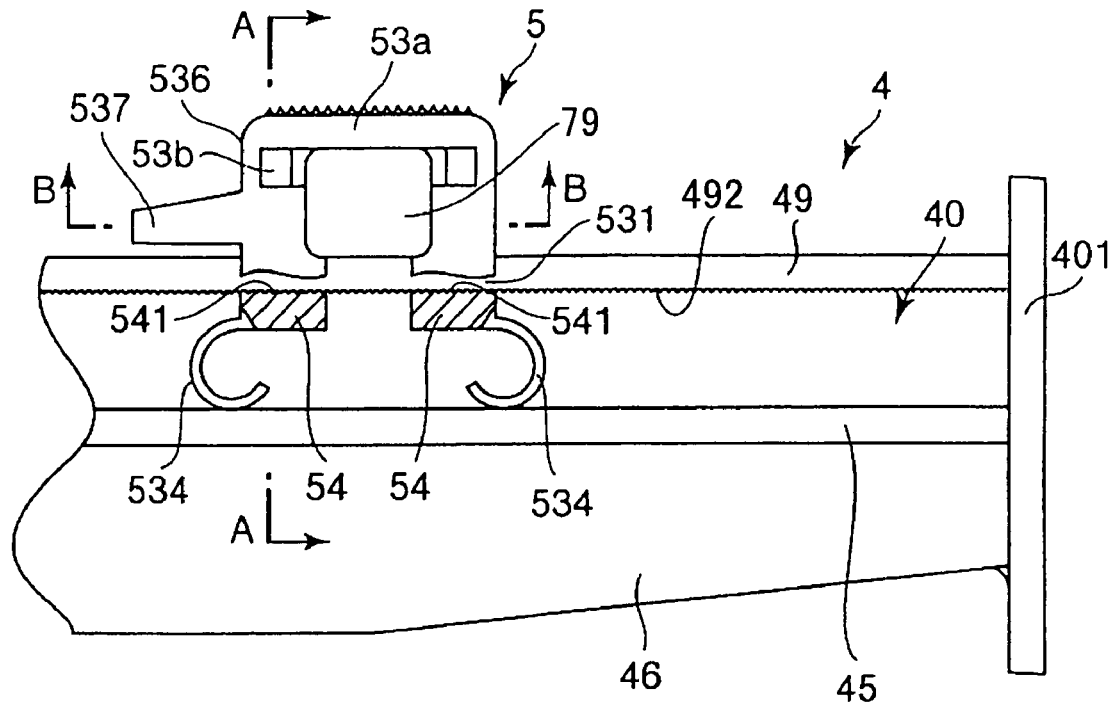
FIGS. 15A-15B shows partly sectional side views illustrating the operating conditions of a stopper attached to the pusher portion shown in FIG. 14.

With each brake portion 54 pressed against the rail portion 49, the stopper 5 is fixed relative to the pusher 4 (the condition shown in FIG. 15A and FIG. 16A).

Figure 15B:
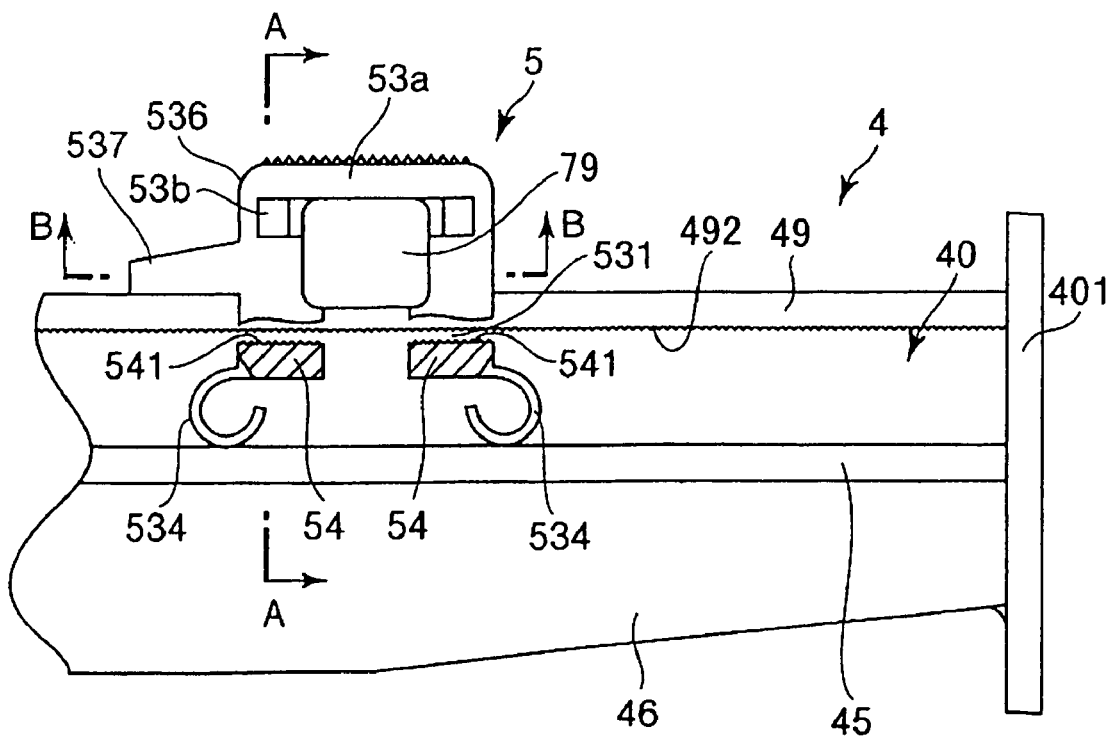

On the other hand, with each brake portion 54 spaced from the rail portion 49, the fixation of the stopper 5 relative to the pusher 4 is released (canceled) (the condition shown in FIG. 15B and FIG. 16B). In this condition, the stopper 5 can be smoothly moved along the longitudinal direction of the pusher 4.

Thus, in this embodiment, lower surfaces 492 of both end portions (left and right end portions, in FIG. 16) of the rail portion 49 and upper surfaces 541 of the brake portions 54 constitute contact surfaces which are pressed against each other. Incidentally, since the rail portions 49 are plate piece-formed as above-mentioned, a pair of the contact surfaces on the side of the pusher 4 are provided to be substantially parallel and are provided on the same plane.

The upper surfaces 541 of the brake portions 54 and the lower surface 492 are both constituted of rough surfaces, in the same manner as in the fifth embodiment. This makes it possible to fix the stopper 5 relative to the pusher 4 more securely.

Incidentally, only one of the upper surface 541 of the brake portion 54 and the lower surface 492 of the rail portion 49 (namely, the contact surfaces of the stopper 5 and the pusher 4) may be constituted of a rough surface. In addition, either one or both of the upper surface 541 of the brake portion 54 and the lower surface 492 of the rail portion 49 may be formed of a material having a high frictional resistance (e.g., an elastic material such as various rubbers, various thermoplastic elastomers, etc.).

In the stopper 5, an operating member 75 for fixing the stopper 5 relative to the pusher 4 is provided to be slidable (displaceable) in the width direction of the pusher 4.

The operating member 75 includes a plate-like (or rod-like) main body portion 78, and is disposed in the condition where the main body portion 78 is inserted between the stopper main body 53 and the rail portions 49 from a lateral side. At both end portions (both left and right end portions, in FIGS. 16 and 17) of the main body portion 78, operating portions 79 each functioning as a pushbutton are provided.

Incidentally, as shown in FIG. 17, a pair of wedge portions (fitting portions) 781 are projected from both end portions (upper and lower portions, in FIG. 17) of the main body portion 78. On the other hand, a pair of thick portions 535 are projected from the surface of the stopper main body 53 on the side of a groove 531 (see FIG. 16). Each wedge portion 781 and each thick portion 535 are provided at substantially the same position, in the longitudinal direction of the pusher 4.

The thickness of the wedge portion 781 is set to be slightly greater than the distance over which the stopper main body 53 can be moved relative to the pusher 4 in the thickness direction of the wedge portion 781 (the direction perpendicular to the longitudinal direction of the pusher 4). Therefore, when the operating portion 79 on one side (the left side, in the configuration shown in the figures) of the operating member 75 is pressed toward the pusher 4, the operating member 75 is slid (displaced) rightwards relative to the stopper 5, and the wedge portion 781 is fitted between the thick portion 535 (stopper main body 53) and the rail portions 49, whereby the stopper main body 53 is moved in the direction of spacing away from the pusher 4. In this instance, each brake portion 54 approaches the rail portion 49, and each brake portion 54 is pressed against the rail portion 49, whereby the stopper 5 is fixed relative to the pusher 4 (see FIGS. 15A, 16A, and 17A).

On the other hand, when the operating portion 79 on the other side (right side, in the configuration shown in the figures) of the operating member 75 is pressed toward the pusher 4 (is pushed back reversely to the above) starting from this condition, the operating member 75 is slid (displaced) leftwards relative to the stopper 5, and the wedge portion 781 is released from between the thick portion 535 (stopper main body 53) and the rail portion 49. As a result, the fixation of the stopper 5 relative to the pusher 4 is released (canceled), and the stopper 5 is slidable (movable) in the longitudinal direction of the pusher 4.

In addition, the surfaces of the wedge portion 781 and the thick portion 535 which face each other in the condition where the fixation of the stopper 5 relative to the pusher 4 is released (canceled) are inclined surfaces 781a and 535a, respectively. This ensures that the operation of fitting the wedge portion 781 between the thick portion 535 (stopper main body 53) and the rail portion 49 can be performed more smoothly and securely.

In the syringe 1 according to the sixth embodiment, the depth of insertion of the pusher 4 into the outer tube 2 is restricted by the abutment of a tip end face 536 of the stopper 5 (stopper main body 53) on the base end portion 28 of the outer tube 2.

In addition, a pair of roughly L-shaped arm portions 537 are provided at the tip ends of the stopper 5. Each arm portion 537 is formed integral with the stopper main body 53 so as to project in the tip end direction from the tip end of the stopper main body 53. In the same manner as in the fifth embodiment, the base end face 421 of the second flange 42 is located at a position corresponding to 0 (zero) of the graduations 48, and the stopper 5 can be easily adjusted to 0 (zero) of the graduations 48 (zero point setting), by moving the stopper 5 in the tip end direction until the tip end of each arm portion 537 abuts on the base end face 421 of the second flange 42. Namely, in this embodiment, each arm portion 537 and the second flange 42 constitute the positioning means for positioning the stopper 5 to 0 (zero) of the graduations 48.

With the syringe 1 according to the sixth embodiment, also, the same functions and effects as those of the syringe 1 according to the fifth embodiment can be obtained. Besides, the syringe 1 according to the sixth embodiment can be used in substantially the same manner as the syringe 1 according to the fifth embodiment.

Seventh Embodiment

Figure 18:
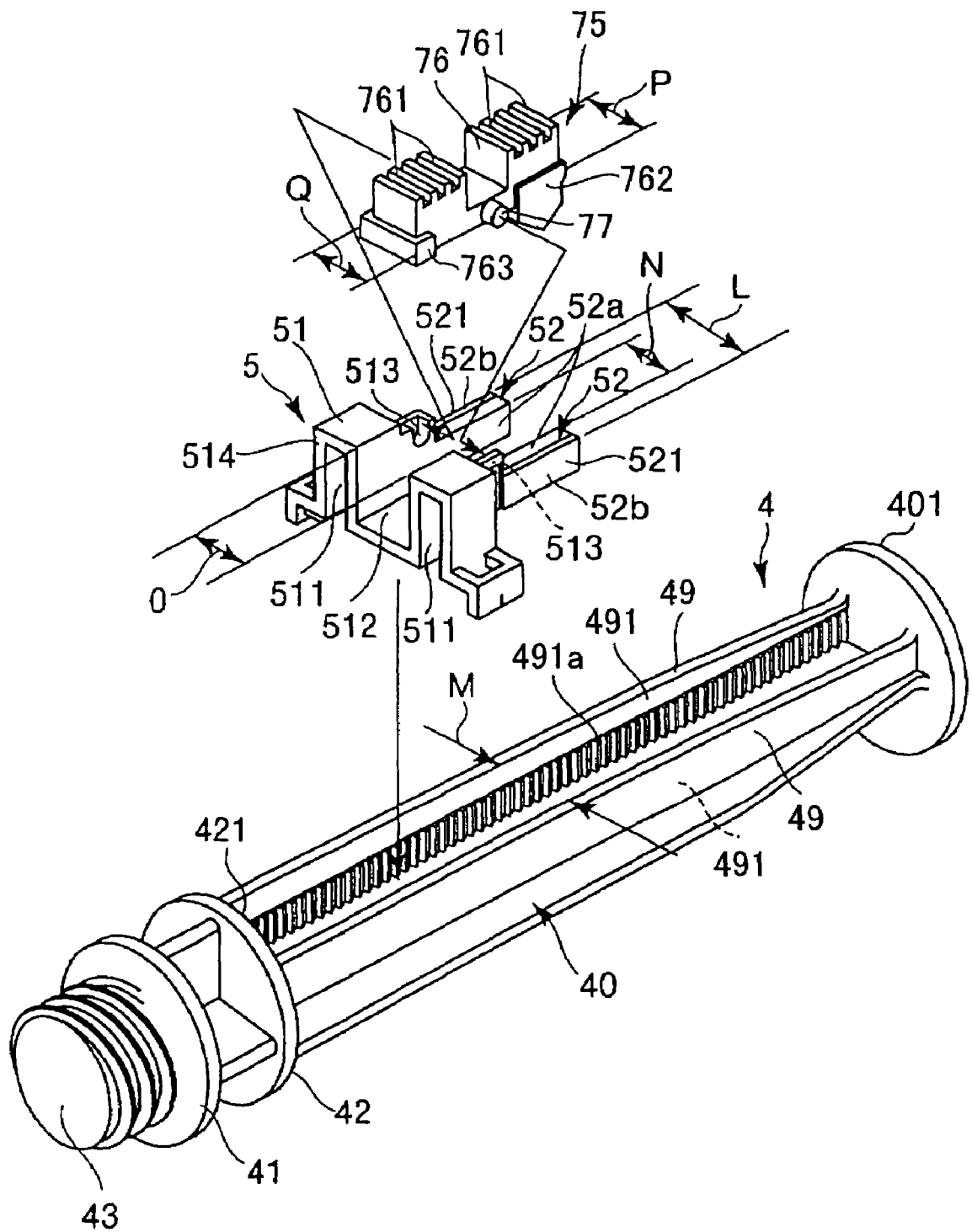
FIG. 18 is an exploded perspective view of a pusher portion in a seventh embodiment of the syringe according to the present invention.

FIG. 18 is an exploded perspective view of a pusher portion in a seventh embodiment of the syringe according to the present invention. Incidentally, for convenience of description, the side of a head (connection portion) of the pusher in FIG. 18 will be referred to as "tip end", and the side of a flange-formed finger receiving portion as "base end".

Now, the syringe according to the seventh embodiment will be described below. In the following, description will be centered on differences from the fifth and sixth embodiments, and description of the same items as above will be omitted.

The seventh embodiment is the same as the fifth embodiment, except for the configurations of the contact surfaces of the stopper and the pusher.

As shown in FIG. 18, each brake portion 52 is composed of an inner member 52a formed integral with a stopper main body 51, and an outer member (pad 52b) attached (fixed) to the outside (the side facing the inner surface 491 of a rail portion 49) of the inner member 52a. The outer member 52b is formed of an elastic material. In other words, the outer surface 521 of each brake portion 52 (the contact surface on the side of the stopper 5) is constituted of a material having a high frictional resistance.

Examples of such a material include various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, and mixtures thereof.

On the other hand, the inner surface 491 of each rail portion 49 is provided with a plurality of recessed portions 491a at a predetermined interval. In this embodiment, the recessed portions 491a are composed of substantially V-shaped grooves.

This configuration ensures that, when the base end side of an operating member 75 (main body portion 76) is pressed toward the pusher 4, a wedge portion 762 (a portion of the operating member 75) is inserted (fitted) between the brake portions 52, 52, to press wider the brake portions 52, 52 in the directions for spacing away from each other. As a result, the outer member 52b formed of the elastic material of each brake portion 52 is pressed against the recessed portions 491a of the rail portion 49, whereby the stopper 5 is fixed relative to the pusher 4.

Incidentally, the shape of the recessed portions 491a is not limited to V shape; for example, the recessed portions 491a may be U-shaped, roughly angular U-shaped, semicircular, or holes or the like.

Other than the configuration shown in the figure, a configuration in which the outer surface 521 of each brake portion 52 is provided with recessed portions and the inner surface 491 of each rail portion 49 is formed of an elastic material may also be adopted, and both the outer surface 521 of each brake portion 52 and the inner surface 491 of each rail portion 49 may be formed of an elastic material.

With the syringe 1 according to the seventh embodiment, also, the same functions and effects as those of the syringe 1 according to the fifth embodiment can be obtained. In addition, the syringe 1 according to the seventh embodiment can be used in substantially the same manner as the syringe 1 according to the fifth embodiment.

While the syringe according to the present invention has been described referring to the embodiments shown in the figures, the present invention is not limited to the embodiments. Each of the portions constituting the syringe can be replaced by one having an arbitrary configuration and being capable of displaying a function equivalent to the above-mentioned.

Besides, in the present invention, arbitrary two or more of the configurations according to the above-described embodiments may be combined.

INDUSTRIAL APPLICABILITY

As has been described above, according to the present invention, an accurate amount of a liquid can be discharged by a simple operation, and such a mistake that the discharge amount would be excessive or insufficient can be securely prevented from occurring.

In addition, it is possible to release (cancel) the fixation of a stopper and regulate the position of the stopper on a pusher by a simple operation of only pressing, pulling or pinching an operating portion, and, therefore, the operation of setting the amount of a liquid to be discharged can be performed extremely easily and swiftly.

Besides, when a configuration in which a fixing means for the stopper is elastically returned to a fixation condition upon release of an operation on the operating portion is adopted, the stopper is automatically returned to the fixed state, so that the position of the stopper once set can be prevented from being deviated to produce an error in the set discharge amount.

In addition, when a configuration in which the stopper is fixed relative to the pusher by pressing a portion of the stopper against the pusher is adopted, either one or both of the contact surfaces of the stopper and the pusher may be constituted of rough surfaces or formed of a material having a high frictional resistance, whereby the minimum of the amount of a liquid discharged can be set at a smaller value. This is advantageous, for example, in that the dose of a chemical can be set more finely, and is therefore suitable for dosing a required amount of a chemical while performing a fine adjustment, as in the case of dosing an antitumor agent.

Besides, in the operation of discharging a liquid, the above-mentioned effects can be attained by a simple operation of only moving the pusher in the tip end direction until the stopper abuts on the outer tube, so that the pusher can be operated without need for subtle regulation of force, which promises excellent operationality.

The invention claimed is:

1. A syringe comprising:
 an outer tube,
 a gasket slidable in said outer tube,
 a pusher inserted through an opening of a base end of said outer tube and operable for moving said gasket,
 a stopper provided on said pusher so that said stopper can be slid along the longitudinal direction of said pusher and the position of said stopper on said pusher can be regulated to a desired position, the stopper is provided with a pair of abutment surfaces,
 an operating member provided to be displaceable relative to said stopper, said operating member performing an operation of fixing said stopper relative to said pusher by pressing a portion of said stopper against said pusher,
 wherein the depth of insertion of said pusher into said outer tube is restricted by abutment of said stopper on a portion of said outer tube,
 wherein said pusher is provided with a pair of abutment surfaces substantially parallel to each other,
 wherein either one or both of the abutment surfaces of said stopper and said pusher are formed as rough surfaces or are formed of a material having a high frictional resistance, and
 wherein said stopper comprises a stopper main body, and a brake portion pressed against said pusher by operation of said operating member, and wherein said pressing of said brake portion against said pusher is performed by clamping said brake portion between a portion of said operating member and said pusher.

2. A syringe as set forth in claim 1, wherein said material having a high frictional resistance is an elastic material.

3. A syringe as set forth in claim 1, wherein said pusher is provided thereon with graduations for indicating the position of said stopper corresponding to the amount of liquid discharged.

4. A syringe as set forth in claim 1, wherein said pusher is provided thereon with graduations for indicating the position of said stopper corresponding to the amount of liquid discharged, and wherein said pusher comprises positioning means for positioning said stopper at the position of 0 (zero) of said graduations.

5. A syringe as set forth in claim 1, wherein a chemical is preliminarily contained in a space surrounded by said outer tube and said gasket.

6. A syringe as set forth in claim 1, wherein the brake portion comprises two spaced apart plates, and the operating member is movable between a first position where a portion of the operating member is positioned between the two plates at a position urging the two plates away from each other and into engagement with the abutment surfaces of the pusher to fix the stopper against movement relative to the pusher, and a second position displaced from the first position in which the portion of the operating member is positioned relative to the two plates in a manner permitting the sliding movement of the stopper relative to the pusher.

7. A syringe as set forth in claim 1, wherein:
 the pusher comprises two rail portions defining a channel extending in a longitudinal direction of the pusher;
 the brake portion comprises two plates spaced from each other and adapted to slide within the channel;
 the operating member comprises a wedge portion adapted to deflect the two flat plate forms of the brake portion in a manner that the two plate forms contact the rail portions to fix the position of the stopper relative to the pusher.

8. A syringe comprising:
 an outer tube,
 a gasket slidable in said outer tube,
 a pusher inserted through an opening of a base end of said outer tube and operable for moving said gasket,
 a stopper provided on said pusher and slidable along the longitudinal direction of said pusher to regulate a position of said stopper along said pusher,
 an operating member displaceable relative to said stopper to fix said stopper relative to said pusher by pressing a portion of said stopper against said pusher,
 a depth of insertion of said pusher into said outer tube being restricted by abutment of said stopper on a portion of said outer tube,
 said pusher comprising a pair of abutment surfaces substantially parallel to each other,
 wherein the abutment surfaces of said pusher have a higher coefficient of friction than an adjoining portion of the pusher, and
 wherein said stopper comprises a stopper main body and a brake portion pressed against said pusher by an operation of said operating member, the brake portion comprising two plates, and the operating member being displaceable relative to the stopper between a first position in which a portion of the operating member is positioned between the two plates at a position urging the two plates away from each other and into engagement with the abutment surfaces of the pusher to fix the stopper against movement relative to the pusher, and a second position displaced from the first position in which the portion of the operating member is positioned relative to the two plates in a manner permitting the sliding movement of the stopper relative to the pusher.

9. The syringe of claim 8 wherein the pusher includes two rail portions extending along a longitudinal direction of the pusher, each rail portion includes one of the abutment surfaces of the pusher, and the abutment surfaces are arranged in facing disposition to one another.

10. The syringe of claim 9 wherein the stopper main body comprises a pair of grooves, each groove receiving a respective rail portion of the pusher such that the stopper is adapted to move along the longitudinal direction of the pusher.

11. The syringe of claim 8 wherein the two plates of the brake portion include outer surfaces adapted to contact the abutment surfaces of the pusher, and the outer surface of each plate has a higher coefficient of friction than an adjoining portion of each plate.

12. The syringe of claim 8 wherein the operating member comprises a pair of laterally projecting rotary shafts, and the stopper main body comprises a pair of bearings receiving the shafts of the operating member, so that the operating member is pivotally mounted on the stopper main body.

* * * * *

UNITED STATES PATENT AND TRADEMARK OFFICE
CERTIFICATE OF CORRECTION

| | |
|---|---|
| PATENT NO. | : 7,427,276 B2 |
| APPLICATION NO. | : 11/878143 |
| DATED | : September 23, 2008 |
| INVENTOR(S) | : Kouichi Tachikawa et al. |

Page 1 of 1

It is certified that error appears in the above-identified patent and that said Letters Patent is hereby corrected as shown below:

Column 5, Line 41: change "outer tube)$_2$" to --outer tube) 2--.

Signed and Sealed this

Seventeenth Day of March, 2009

JOHN DOLL
*Acting Director of the United States Patent and Trademark Office*